United States Patent
Lennon et al.

(10) Patent No.: US 12,105,088 B2
(45) Date of Patent: Oct. 1, 2024

(54) METHODS AND MATERIALS FOR IDENTIFYING AND TREATING AUTOIMMUNE GFAP ASTROCYTOPATHY

(71) Applicant: Mayo Foundation for Medical Education and Research, Rochester, MN (US)

(72) Inventors: Vanda A. Lennon, Rochester, MN (US); Andrew McKeon, Rochester, MN (US); Boyan Fang, Rochester, MN (US); Shannon Hinson, Rochester, MN (US); Thomas J. Kryzer, Mantorville, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 146 days.

(21) Appl. No.: 17/870,477

(22) Filed: Jul. 21, 2022

(65) Prior Publication Data
US 2022/0357322 A1    Nov. 10, 2022

Related U.S. Application Data

(62) Division of application No. 16/331,853, filed as application No. PCT/US2017/050252 on Sep. 6, 2017, now Pat. No. 11,402,379.

(60) Provisional application No. 62/385,467, filed on Sep. 9, 2016.

(51) Int. Cl.
G01N 33/53    (2006.01)
A61K 49/06    (2006.01)
G01N 33/564   (2006.01)

(52) U.S. Cl.
CPC .......... *G01N 33/564* (2013.01); *A61K 49/06* (2013.01); *G01N 2800/24* (2013.01)

(58) Field of Classification Search
CPC .... G01N 33/53; G01N 33/543; G01N 33/564; G01N 2800/24; Y10S 436/808
See application file for complete search history.

(56) References Cited

U.S. PATENT DOCUMENTS

| | | | |
|---|---|---|---|
| 5,420,016 A * | 5/1995 | Boguslaski | C12Q 1/04 435/12 |
| 6,372,808 B1 | 4/2002 | Kanada et al. | |
| 11,402,379 B2 | 8/2022 | Lennon et al. | |
| 2003/0157580 A1 | 8/2003 | Hochstrasser et al. | |
| 2006/0134108 A1 | 6/2006 | Jackowski et al. | |
| 2010/0210816 A1 | 8/2010 | Dambinova | |
| 2012/0077686 A1 * | 3/2012 | Weiner | G01N 33/564 506/18 |
| 2012/0114614 A1 * | 5/2012 | Ratajczak | A61K 35/51 435/325 |
| 2015/0233904 A1 * | 8/2015 | Nayak | G01N 33/5308 435/7.92 |
| 2018/0231571 A1 * | 8/2018 | Kim | G01N 33/6896 |
| 2019/0376965 A1 | 12/2019 | Lennon et al. | |

FOREIGN PATENT DOCUMENTS

| | | |
|---|---|---|
| EP | 3018478 | 5/2016 |
| WO | WO 2005/041944 | 5/2005 |
| WO | WO 2005/048807 | 6/2005 |
| WO | WO 2011/032155 | 3/2011 |
| WO | WO 2011/123844 | 10/2011 |
| WO | WO 2011/160096 | 12/2011 |
| WO | WO 2013/138509 | 9/2013 |

OTHER PUBLICATIONS

Wei et al., Serum GFAP autoantibody as an ELISA-detectable glioma marker, Tumor Biol, 2013, 34, pp. 2283-2292. (Year: 2013).*
Peery et al., Anti-NMDA receptor encephalitis. The disorder, the diagnosis and the immunobiology, Autoimmunity Reviews, 11, 2012, pp. 863-872. (Year: 2012).*
Catiillo-Gomez et al., The Brain as Immunoprecipitatior of serum autoantibodies against N-Methyl-D-Aspartate Receptor Subunit NR1, Annals of Neurology, 79(1), Jan. 2016, pp. 144-151. (Year: 2016).*
Takahashi et al., Anti-aquaporin-4 antibody is involved in the pathogenesis of NMO: a study on antibody titre, Brain, 2007, 130; pp. 1235-1243. (Year: 2007).*
Tanaka et al., Enzynme-lined immunosorbent assay for human autoantibody to glial fibrillary acidic protein: higher titer of the antibody is detected in serum of patients with Alzheimer's disease, Acta Neurol. Scanc., 1989, 80, pp. 554-560. (Year: 1989).*
Abou-Donia et al., "Autoantibody markers of neural degeneration are associated with post-mortem histopathological alterations of a neurologically-injured pilot," J. Biol. Phys. Chem, 14:34-53, 2014.
Albert et al., "Tumor-specific killer cells in paraneoplastic cerebellar degeneration," Nat. Med., 4(11):1321-4, Nov. 1998.
Blechingberg et al., "Regulatory mechanisms for 3'-end alternative splicing and polyadenylation of the Glial Fibrillary Acidic Protein, GFAP, transcript," Nucleic Acids Res., 35(22):7636-50, Nov. 2007.
Cayre et al., "Cell migration in the normal and pathological postnatal mammalian brain," Prog. Neurobiol., 88(1): 41-63, May 2009.
Crisp et al., "Autoimmune synaptopathies," Nat. Rev. Neurosci., 17(2):103-17, Jan. 2016.
Dalmau and Rosenfeld, "Autoimmune encephalitis update," Neuro. Oncol., 16(6):771-8, Mar. 2014.

(Continued)

*Primary Examiner* — Gary Counts
(74) *Attorney, Agent, or Firm* — Fish & Richardson P.C.

(57) ABSTRACT

This document provides methods and materials involved in identifying and treating autoimmune GFAP (glial fibrillary acidic protein) astrocytopathy, a novel meningoencephalomyelitis, in humans as well as methods and materials for identifying and offering early treatment for patients having autoimmune GFAP astrocytopathy whose autoantibody profile predicts a high likelihood of having underlying cancer (e.g., adenocarcinoma or teratoma).

8 Claims, 16 Drawing Sheets

(56) References Cited

OTHER PUBLICATIONS

Dalmau et al., "Clinical experience and laboratory investigations in patients with anti-NMDAR encephalitis," Lancet Neurol., 10(1):63-74, Jan. 2011.
Extended European Search Report in European Application No. 17849443.1 dated May 15, 2020, 11 pages.
Fang et al., "Autoimmune GFAP Astrocytopathy: A Novel Meningoencephalomyelitis," JAMA Neurol., 73(11):1297-307, Nov. 2016.
Farina et al., "Can MR imaging diagnose adult-onset Alexander disease?" Am. J. Neuroradiol., 29(6): 1190-6., Jun. 2008.
Flanagan et al., "Discriminating long myelitis of neuromyelitis optica from sarcoidosis," Ann. Neurol., 79(3): 437-47, Mar. 2016.
Flanagan et al., "Glial fibrillary acidic protein immunoglobulin G as biomarker of autoimmune astrocytopathy: Analysis of 102 patients" Ann. Neurol., 81(2):298-309, Feb. 2017.
Fujihara et al., "Neuromyelitis optica should be classified as an astrocytopathic disease rather than a demyelinating disease," Clinical and Experimental Neuroimmunology, 3(2):58-73, May 2012.
Ganta et al., "Radial contrast enhancement on brain magnetic resonance imaging diagnostic of primary angiitis of the central nervous system: a case report and review of the literature," J. Med. Case Rep., 8(1):26, Dec. 2014.
GenBank Accession No. NM_001317384.1, "*Homo sapiens* aquaporin 4 (AQP4), transcript variant 1, mRNA," Dec. 20, 2017, 5 pages.
GenBank Accession No. NP_001304313.1, "aquaporin-4 isoform M1x [*Homo sapiens*]," Jan. 13, 2018, 3 pages.
Hassan et al., "Linear magnetic resonance enhancement and optic neuropathy in primary angiitis of the central nervous system," J. Neuroophthalmol., 23(2):127-31, Jun. 2003.
Heo et al., "A histopathological diagnostic marker for human spinal astrocytoma: expression of glial fibrillary acidic protein-delta," J. Neurooncol., 108(1):45-52, Feb. 2012.
Higgins et al., "Brain Tumor Stem Cell Multipotency Correlates with Nanog Expression and Extent of Passaging in Human Glioblastoma Xenografts," Oncotarget., 4(5):792-801, Jun. 2013.
Horta et al., "Neural Autoantibody Clusters Aid Diagnosis of Cancer" Clin. Cancer Res., 20(14):3862-9, Jul. 2014.
Iorio and Lennon, "Neural antigen-specific autoimmune disorders," Immunol. Rev., 248(1):104-21, Jun. 2012.
Kamchatnov et al., "Autoantibodies to GFAP (glial fibrillary acidic protein) and to dopamine in patients with acute and chronic cerebrovascular disorder" Health, 2(12):1366-71, 2017.
Linnoila et al., "CSF herpes virus and autoantibody profiles in the evaluation of encephalitis," Neurol. Neuroimmunol. Neuroinflamm., 3:e245, Jun. 2016.
Majed et al., "Clinical utility of testing AQP4-IgG in CSF: Guidance for physicians," Neurol. Neuroimmunol. Neuroinflamm., 3(3):e231, Apr. 2016.
McKeon et al., "Paraneoplastic encephalomyelopathies: pathology and mechanisms," Acta Neuropathol., 122(4):381-400, Sep. 2011.
McKeon et al., "Purkinje Cell Cytoplasmic Autoantibody Type 1 Accompaniments: The Cerebellum and Beyond," Arch. Neurol., 68(10):1282, Oct. 2011.
Meeusen et al., "Potassium channel complex autoimmunity induced by inhaled brain tissue aerosol," Ann. Neurol., 71(3):417-26, 2012.
Middeldorp and EM, "GFAP in health and disease," Prog. Neurobiol., 93(3):421-43, Mar. 2011.
O'Toole et al., "Autoimmune chorea in adults," Neurology, 80(12):1133-44, Feb. 2013.
PCT International Preliminary Report on Patentability in International Appln. No. PCT/US2017/050252 dated Mar. 21, 2019, 8 pages.
PCT International Search Report and Written Opinion in International Appln. No. PCT/US2017/050252 dated Nov. 16, 2017, 10 pages.
Petzold, "Glial fibrillary acidic protein is a body fluid biomarker for glial pathology in human disease," Brian Res., 1600:17-31, 2015.
Pittock et al., "Chronic lymphocytic inflammation with pontine perivascular enhancement responsive to steroids (CLIPPERS)," Brain, 133(9):2626-34, Sep. 2010.
Pittock et al., "Paraneoplastic antibodies coexist and predict cancer, not neurological syndrome," Ann. Neurol., 56(5):715-9, Oct. 2004.
Ramamoorthy and Cidlowski, "Corticosteroids: Mechanisms of Action in Health and Disease," Rheum. Dis. Clin. North Am., 42(1):15-31, Feb. 2016.
Roelofs et al., "Adult human subventricular, subgranular, and subpial zones contain astrocytes with a specialized intermediate filament cytoskeleton," Glia, 52(4):289-300, Jul. 2005.
Salvarani et al., "Angiography-negative primary central nervous system vasculitis: a syndrome involving small cerebral vessels," Medicine, 87(5):264-71, Sep. 2008.
Sasaki et al., "Relapsing-remitting central nervous system autoimmunity mediated by GFAP-specific CD8 T cells," J. Immunol., 192(7):3029-42, Apr. 2014.
Schweingruber et al., "Chemokine-mediated redirection of T cells constitutes a critical mechanism of glucocorticoid therapy in autoimmune CNS responses," Acta Neuropathol., 127(5):713-29, Feb. 2014.
Shibuya et al., "Autoantibodies against glial fibrillary acidic protein (GFAP) in cerebrospinal fluids from Pug dogs with necrotizing meningoencephalitis," J. Vet. Med. Sci., 69(3):241-5, 2007.
Shoemaker et al., "Primary angiitis of the central nervous system: unusual MR appearance," Am. J. Neuroradiol., 15(2):331-4, Feb. 1994.
Singh et al., "Circulating autoantibodies to neuronal and glial filament proteins in autism," Pediatric neurology, 17(1):88-90, Jul. 1997.
Tachibana et al., "Expression of various glutamate receptors including N-methyl-D-aspartate receptor (NMDAR) in an ovarian teratoma removed from a young woman with anti-NMDAR encephalitis," Intern. Med., 49(19):2167-73, 2010.
Tateishi et al., "MR imaging of the brain in lymphomatoid granulomatosis," Am. J. Neuroradiol., 22(7):1283-90, Aug. 2001.
Toledano et al., "Utility of an immunotherapy trial in evaluating patients with presumed autoimmune epilepsy," Neurology, 82(18):1578-86, May 2014.
Vance et al., "Immature neural elements in immature teratomas. An immunohistochemical and ultrastructural study," Am. J. Clin. Pathol., 90(4):397-411, Oct. 1988.
Venkatesan et al., "Case Definitions, Diagnostic Algorithms, and Priorities in Encephalitis: Consensus Statement of the International Encephalitis Consortium," Clin. Infect. Dis., 57(8):1114-28, Jul. 2013.
Williams et al., "Association of Autoimmune Encephalitis With Combined Immune Checkpoint Inhibitor Treatment for Metastatic Cancer.," JAMA Neurol., 73(8):928-33, 2016.
Williams et al., "Neurosarcoidosis: gadolinium-enhanced MR imaging," J. Comput. Assist. Tomogr., 14(5):704-7, Sep. 1990.
Zalewski et al., "Central canal enhancement and the trident sign in spinal cord sarcoidosis," Neurology, 87(7): 743-4, Aug. 2016.
Zalewski et al., "P/Q- and N-type calcium-channel antibodies: Oncological, neurological, and serological accompaniments," Muscle Nerve, 54(2):220-7, Jan. 2016.
Zhang et al., "Human Traumatic Brain Injury Induces Autoantibody Response against Glial Fibrillary Acidic Protein and Its Breakdown Products," PLoS One, 9:e92698, Mar. 2014.

\* cited by examiner

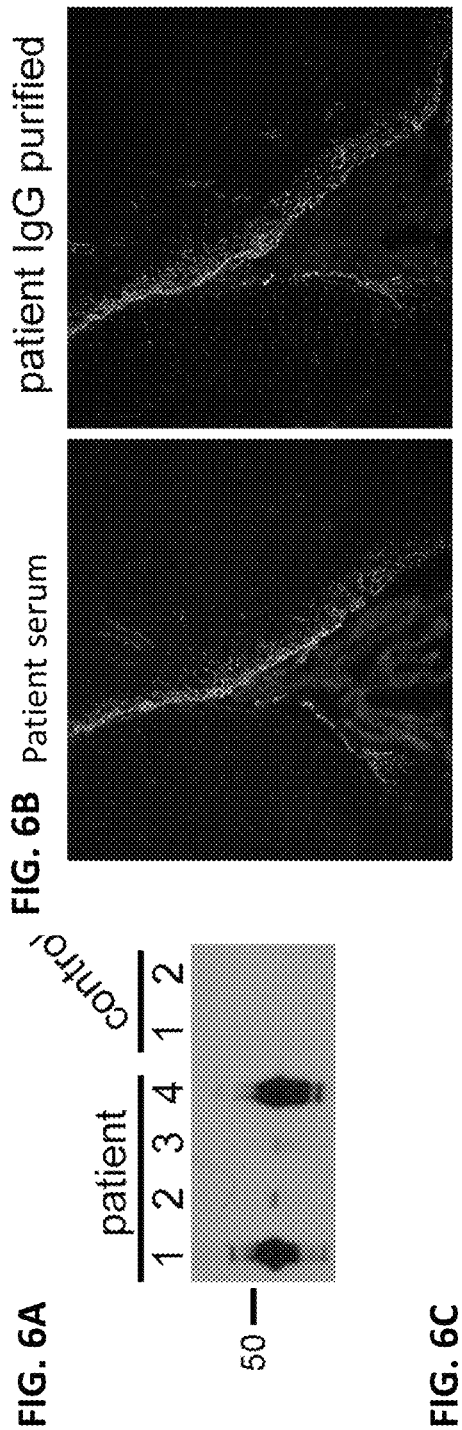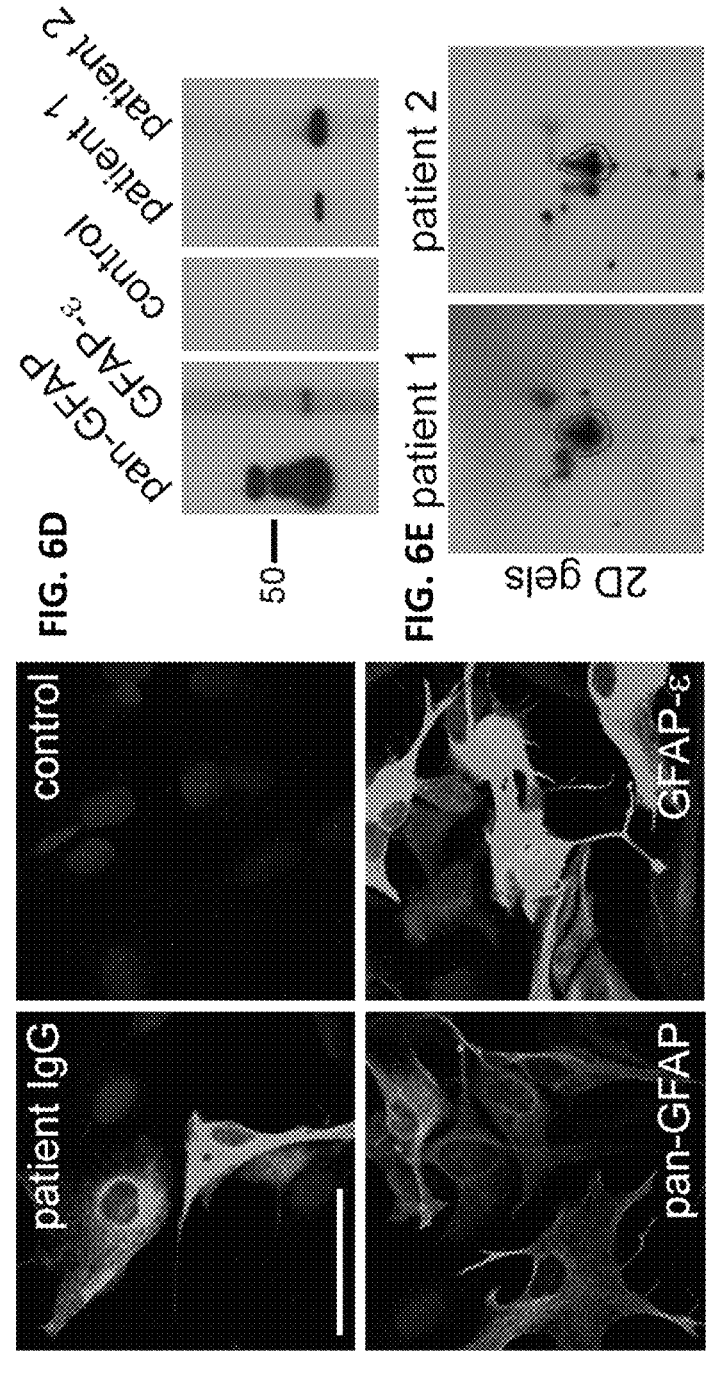

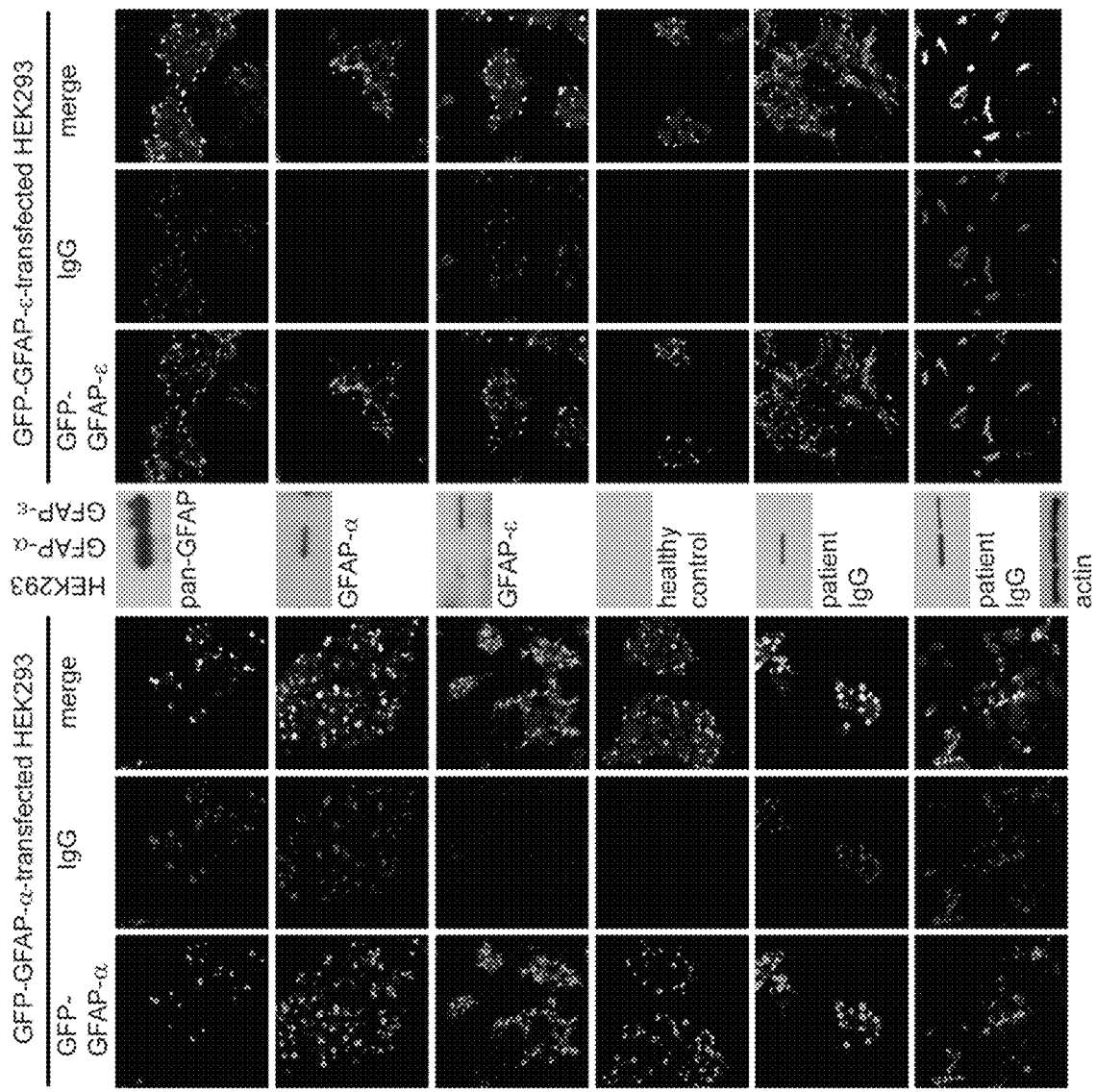

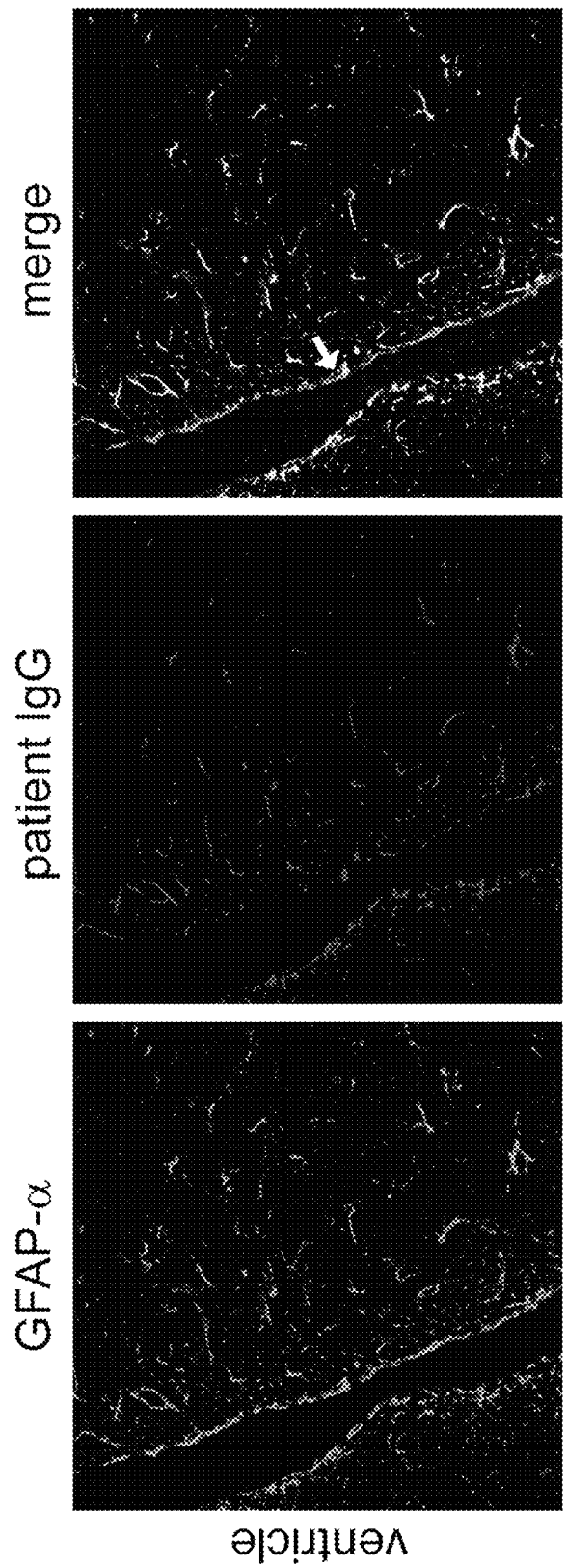

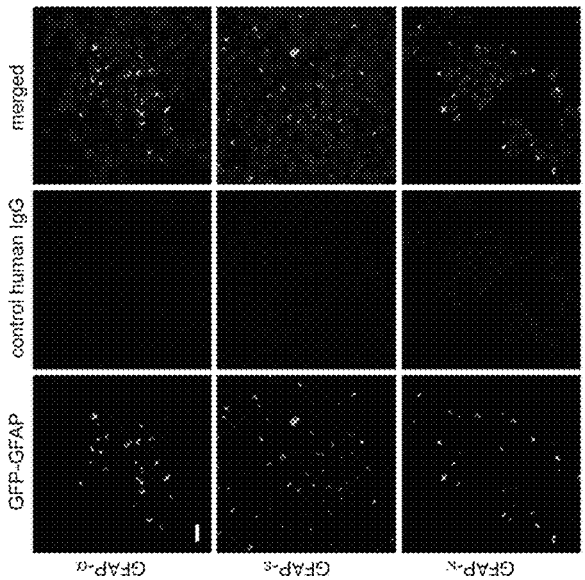
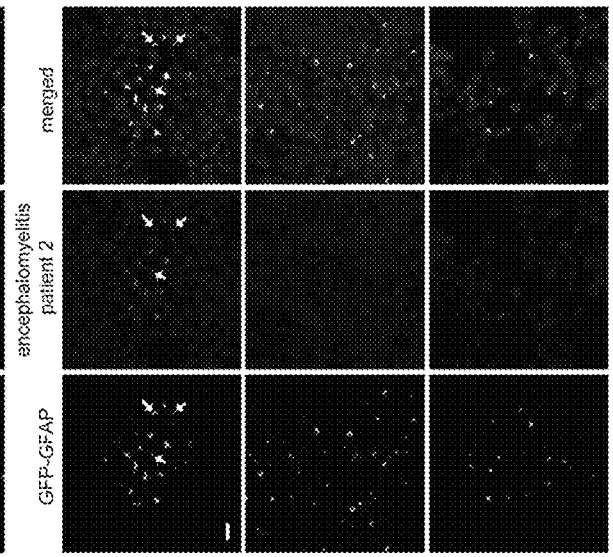
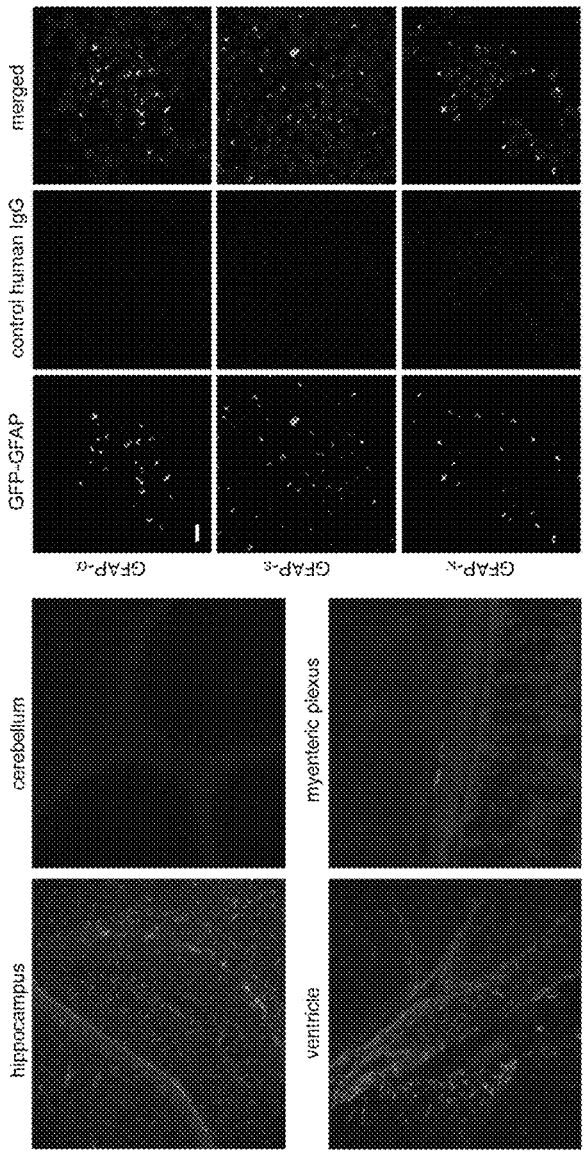
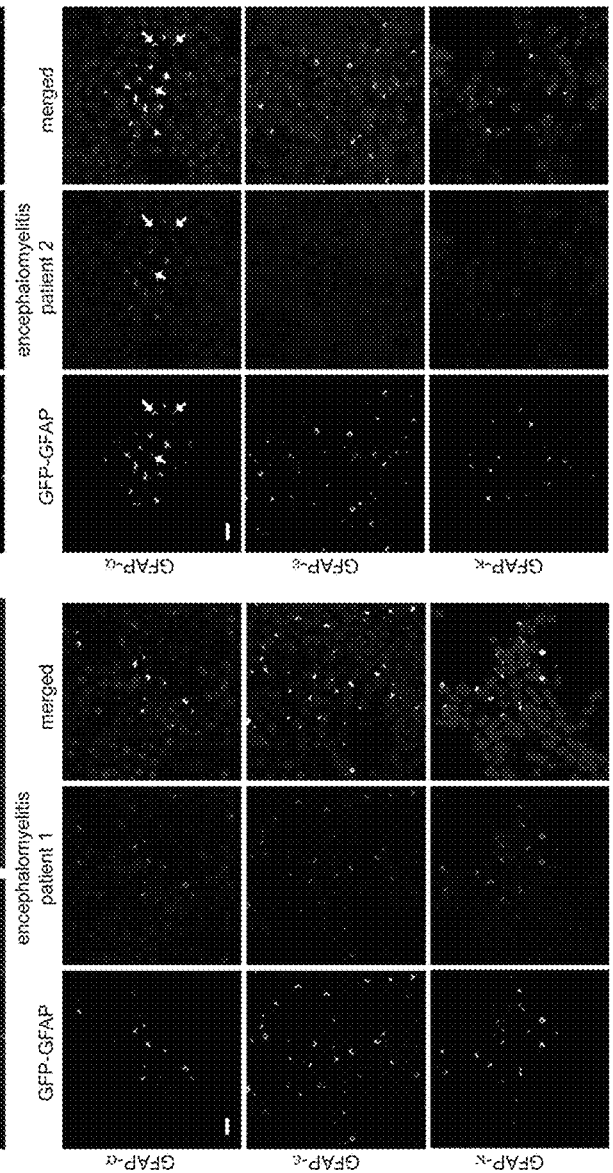

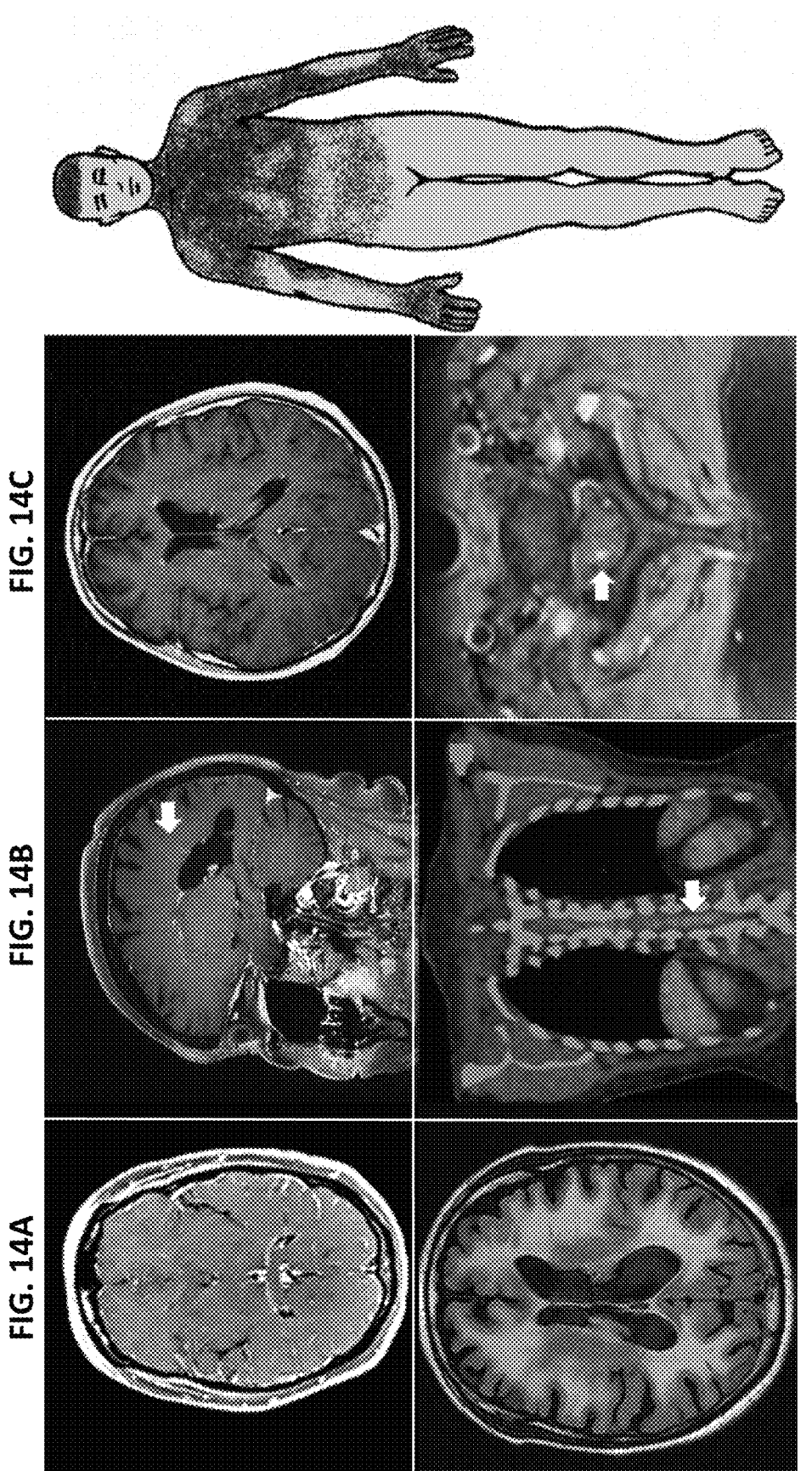

METHODS AND MATERIALS FOR IDENTIFYING AND TREATING AUTOIMMUNE GFAP ASTROCYTOPATHY

CROSS-REFERENCE TO RELATED APPLICATIONS

This application is a divisional of U.S. application Ser. No. 16/331,853, filed Mar. 8, 2019, (now U.S. Pat. No. 11,402,379), which is a National Stage application under 35 U.S.C. § 371 of International Application No. PCT/US2017/050252, having an International Filing Date of Sep. 6, 2017, which claims the benefit of priority to U.S. Provisional Application Ser. No. 62/385,467, filed Sep. 9, 2016. The disclosure of the prior applications are considered part of (and are incorporated by reference in) the disclosure of this application.

BACKGROUND

1. Technical Field

This document relates to methods and materials involved in identifying and treating autoimmune GFAP (glial fibrillary acidic protein) astrocytopathy in humans, a novel meningoencephalomyelitis in humans, as well as methods and materials for identifying and treating humans having autoimmune GFAP astrocytopathy with underlying cancer (e.g., one or more teratomas).

2. Background Information

Neural antigen-specific autoimmune disorders can impact all nervous system levels (Iorio and Lennon, *Immunol. Rev.*, 248(1):104-21 (2012); Dalmau and Rosenfeld, *Neuro. Oncol.*, 16(6):771-8 (2014); and Crisp et al., *Nat. Rev. Neurosci.*, 17(2):103-17 (2016)). Subacute or insidious symptom onset raises suspicion for an infectious, degenerative, demyelinating, neoplastic, or vascular disorder. Detection in serum or CSF of neuronal, glial, or skeletal muscle-specific IgGs can aid diagnosis and guide appropriate therapeutic options. Paraneoplastic cases reflect immune responses incited by onconeural antigens in an occult systemic cancer. Informative autoantibody profiles predict high cancer probability (Pittock et al., *Ann. Neurol.*, 56(5):715-9 (2004); and Horta et al., *Clin. Cancer Res.*, 20(14):3862-9 (2014)) and may yield immunopathogenic insights.

SUMMARY

This document provides methods and materials involved in identifying and treating autoimmune GFAP astrocytopathy in humans, a novel meningoencephalomyelitis in humans. For example, this document provides methods and materials for detecting GFAP-specific IgG autoantibodies to identify humans as having autoimmune GFAP astrocytopathy. Once identified as having autoimmune GFAP astrocytopathy, the human can be treated with immunosuppressant therapy (e.g., corticosteroid such as initial high dose corticosteroid therapy) followed long-term by a corticosteroid-sparing drug such as mycophenolate mofetil or azathioprine.

As described herein, the presence of GFAP-specific IgG autoantibodies in a biological sample (e.g., a serum sample or a cerebrospinal fluid (CSF) sample) obtained from a human can indicate that that human has autoimmune GFAP astrocytopathy. Humans identified as having autoimmune GFAP astrocytopathy as described herein can be treated with immunosuppressant therapy (e.g., high dose corticosteroid therapy). Having the ability to identify and/or treat humans with autoimmune GFAP astrocytopathy as described herein can allow clinicians to initiate appropriate treatment protocols quickly and effectively.

This document also provides methods and materials for identifying and treating humans having autoimmune GFAP astrocytopathy as having underlying cancer (e.g., one or more teratomas). For example, this document provides methods and materials for detecting GFAP-specific IgG autoantibodies in combination with other IgG autoantibodies (e.g., N-methyl-D-aspartate receptor (NMDA-R)-specific IgG autoantibodies and/or aquaporin-4 (AQP4)-specific IgG autoantibodies) to identify humans having autoimmune GFAP astrocytopathy as being likely to have an underlying cancer (e.g., one or more teratomas). Once a human is identified as being likely to have underlying cancer as described herein, an appropriate diagnostic approach can be used to confirm the present of cancer in the human having autoimmune GFAP astrocytopathy. For example, an appropriate imaging test can be used to confirm that a human identified as being likely to have underlying cancer as described herein has cancer. Once confirmed as having cancer, the human can be treated with an appropriate therapy at an early stage using, for example, surgical resection, chemotherapy, radiation therapy, or combinations thereof.

As described herein, the presence of GFAP-specific IgG in combination with NMDA-R-specific IgG and/or AQP4-specific IgG in a biological sample (e.g., a serum sample or a cerebrospinal fluid (CSF) sample) obtained from a human with autoimmune GFAP astrocytopathy can indicate that that human has an increased likelihood of having an underlying cancer (e.g., one or more teratomas) as compared to humans with autoimmune GFAP astrocytopathy that lack NMDA-R-specific IgG and AQP4-specific IgG. Humans identified as having autoimmune GFAP astrocytopathy with an increased likelihood of having an underlying cancer as described herein can be treated with appropriate oncological therapy (e.g., surgical resection, chemotherapy, radiation therapy, and combinations thereof) and immunotherapy (e.g., corticosteroids plus mycophenolate mofetil or azathioprine). Having the ability to identify and/or treat humans having autoimmune GFAP astrocytopathy with an increased likelihood of having an underlying cancer (e.g., one or more teratomas) as described herein can allow clinicians to initiate appropriate treatment protocols quickly and effectively.

In general, one aspect of this document features a method for identifying a human having an autoimmune GFAP astrocytopathy. The method comprises, or consists essentially of, (a) determining that the human has GFAP-specific IgG, and (b) classifying the human as having the autoimmune GFAP astrocytopathy. The method can be an in vitro method. The method can comprises detecting the presence of the GFAP-specific IgG within a biological sample obtained from the human. The sample can be a cerebrospinal fluid sample.

In another aspect, this document features a method for treating an autoimmune GFAP astrocytopathy in a human. The method comprises, or consists essentially of, (a) identifying the human as having GFAP-specific IgG, and (b) administering a steroid compound to the human. The method can comprises detecting the presence of the GFAP-specific IgG within a biological sample obtained from the human. The sample can be a cerebrospinal fluid sample.

In another aspect, this document features a method for treating an autoimmune GFAP astrocytopathy. The method comprises, or consists essentially of, administering a steroid compound to a human identified as having GFAP-specific IgG. The steroid can be a corticosteroid.

In another aspect, this document features a method for identifying a human having an autoimmune GFAP astrocytopathy as being likely to have an underlying cancer. The method comprises, or consists essentially of, (a) determining that the human has NMDA-R-specific IgG or AQP4-specific IgG, and (b) classifying the human as having a likelihood of the cancer. The cancer can be an adenocarcinoma or teratoma. The method can comprise detecting the presence of the NMDA-R-specific IgG or AQP4-specific IgG within a biological sample obtained from the human. The sample can be a cerebrospinal fluid sample. The method can comprise detecting to presence of the NMDA-R-specific IgG. The method can comprise detecting to presence of the AQP4-specific IgG.

In another aspect, this document features a kit comprising, or consisting essentially of, (a) a first antigen source comprising a GFAP polypeptide and lacking NMDA-R and AQP4 polypeptides, (b) a second antigen source comprising a NMDA-R or AQP4 polypeptide and lacking GFAP polypeptides, and (c) an anti-human IgG antibody. The first antigen source can be a cell transfected to express the GFAP polypeptide. The GFAP polypeptide can be a human GFAP polypeptide. The second antigen source can comprise the NMDA-R polypeptide. The second antigen source can comprise the AQP4 polypeptide. The second antigen source can be a cell transfected to express the NMDA-R or AQP4 polypeptide. The second antigen source can be a cell transfected to express the NMDA-R polypeptide and the AQP4 polypeptide. The NMDA-R polypeptide can be a human NMDA-R polypeptide. The AQP4 polypeptide can be a human AQP4 polypeptide. The anti-human IgG antibody can be covalently attached to a label moiety. The label moiety can be a florescent moiety. The kit can comprise GFAP-specific IgG, NMDA-R-specific IgG, or AQP4-specific IgG.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2A. Distribution of patient IgG (green) in mouse pia/subpia and midbrain parenchyma is consistent with astrocytes (×20). FIG. 2B. Periventricular region (×20). FIG. 2C. Gastric smooth muscle contains immunoreactive ganglia (arrow heads) and nerve bundles and segments, some (arrows) penetrating mucosa (×40). FIG. 2D. Filamentous staining of rat hemi-spinal cord is prominent around the central canal (CC); GM=ventral grey matter and WM=white matter (×20). FIG. 2E. Brain image of patient #7 (FIG. 2E and FIG. 2F (enlarged)) demonstrates prominent radial pattern of periventricular post-gadolinium enhancement (T1, sagittal). Spinal cord of patient #10 (G-I): T2 signal abnormalities are hazy (sagittal, FIG. 2G; axial, FIG. 2I and FIG. 2J), longitudinally-extensive (FIG. 2G), and most prominent centrally (FIG. 2I). Gadolinium enhancement of patient's central spinal cord is prominent and longitudinally extensive in sagittal image (FIG. 2H, arrowheads; T1).

FIG. 5A. GFAP-α and patient IgGs largely co-localize in astrocytes of pia and subpia (×20). FIG. 5B. Unlike GFAP-α IgG, patient IgG is largely non-reactive with radial processes of cerebellar cortical Bergmann glia (×20). FIG. 5C. Both IgGs completely co-localize in myenteric plexus glia (×20). GFAP-δ-IgG and patient IgG co-localize extensively in pia and subpial (FIG. 5D), cerebellum (FIG. 5E; note: neither GFAP-δ-IgG nor patient IgG binds to Bergmann glial processes) and myenteric plexus (FIG. 5F). FIG. 5D. Co-localized IgGs appear yellow in merged panels; DNA is blue (DAPI-stained). Note: "ε", the human GFAP isoform nomenclature, is "δ" in rodents.

FIGS. 6A-6E. Autoantigen identification. FIG. 6A. Western blot of proteins isolated from rat spinal cord probed with IgG from 4 individual patients and 2 healthy controls. Patient IgG binds to an approximately 50 kD band. FIG. 6B. Immunostaining of mouse periventricular region with IgG in original patient serum and with neutralized IgG acid-eluted from non-stained replica of transblotted immunoreactive band. FIG. 6C. Cytoplasm of glioblastoma multiforme (GBM) xenograft cells binds patient IgG, commercial GFAP-IgGs, pan-reactive and ε-isoform-specific (green), but not control human IgG. DNA is stained blue with DAPI. Scale bar 50 μm. FIG. 6D. Western blot of GBM tumor xenograft lysate (8000 g insoluble fraction) probed with commercial GFAP IgGs and healthy control or two patient IgGs. FIG. 6E. GBM lysate proteins separated by 2D electrophoresis and probed with IgG from two patients. Red outline defines the protein identified as GFAP by mass spectrometry analysis. Note: "ε", the human GFAP isoform nomenclature, is "δ" in rodents.

FIG. 7A-7F. IgG binding to HEK293 cells transfected with expression plasmids encoding GFP-tagged human GFAP-α or human GFAP-ε. Analysis by immunofluorescence (fixed, permeabilized cells) and by western blot (post-nuclear cell lysates; actin immunoreactivity (row 7F) confirmed equivalent protein loading). Pan-GFAP-reactive control IgG bound to both α and ε isoforms of GFAP (FIG. 7A). Control IgGs mono-specific for GFAP-α (FIG. 7B) or GFAP-ε (FIG. 7C) isoforms bound selectively to the anticipated protein product. Healthy human control IgG did not bind to non-transfected, GFAP-α or GFAP-ε transfected cells or lysates (FIG. 7D). Examples of patients' IgGs binding to GFAP-α only (FIG. 7E) or both GFAP-α and GFAP-ε (FIG. 7F). Note: "ε", the human GFAP isoform nomenclature, is "δ" in rodents.

FIGS. 9A-9C. Human patient IgG immunoreactivity in GFAP-α-positive ependyma. Dual immunofluorescence staining of mouse brain periventricular region by commercial IgG specific for glial fibrillary acidic protein (GFAP) α isoform (green) and serum IgG of patient with autoimmune GFAP astrocytopathy (red). FIG. 9A. Cytoplasm of ependymocytes as well as subventricular astrocytes is GFAP-α immunoreactive. FIG. 9B. Ependymocytes do not uniformly bind patient IgG. FIG. 9C. Partial co-localization of IgG probes (yellow) is apparent in merged figure. Arrow indicates lack of patient IgG binding to ependyma on right wall of ventricle.

FIGS. 10A-10D. Typical findings for GFAP-IgG localization and isoform specificity by tissue-based and transfected cell-based immunofluorescence assays. (FIG. 10A) Patient IgG binding to mouse tissues is most prominent in hippocampus, ventricular regions and myenteric plexus. Binding to cerebellum is absent. (FIG. 10B-FIG. 10D) HEK293 cells stably expressing GFP-tagged GFAP isoforms: α, ε, and κ (green) immunostained with human IgG (red). Healthy control IgG (FIG. 10B) does not bind; IgG in two patients with autoimmune GFAP astrocytopathy binds in 1 case to 3 isoforms (FIG. 10C), and in the other to 1 isoform (FIG. 10D). Co-localized human IgG and GFAP isoform is yellow in merged images (smaller co-localizing areas indicated with arrows). DNA is stained with DAPI (blue). Scale bars, 20 μm.

FIG. 12B, patient 5) and sagittal images (FIG. 12C, patient 8), and sometimes dotted/punctate in appearance (FIG. 12D, patient 7); some enhancing lesions appeared serpentine on axial images (FIG. 12E, patient 33, arrow) and in sopme, vessel enhancement was noted in the region of the ependyma (FIG. 12F, patient 35, arrows).

FIGS. 14A-G. Patient 1, diffuse leptomeningeal gadolinium enhancement on axial T1 post-contrast MRI (FIG. 14A). Patient 2, radial pattern (arrow) of gadolinium enhancement on sagittal T1 post-contrast MRI (FIG. 14B). Patient 3, punctate periventricular and diencephalic areas of enhancement (FIG. 14C). Patient 4, periventricular and subcortical T2/FLAIR hyperintenisity and atrophy (FIG. 14D). Patient 5, increased FDG uptake in the spinal cord on FDG-PET scan (FIG. 14E). Patient 6, gadolinium enhancement on right lateral aspect (arrow) on the cervical spinal cord FIG. 14 (FIG. 14F). Patient 7, thermoregulatory sweat test, light skin areas indicate reduced or absent heat-induced sweat output (revealed by indicator powder (alizarin red)) in a patient with myelitis (FIG. 14G).

DETAILED DESCRIPTION

Figure 1:
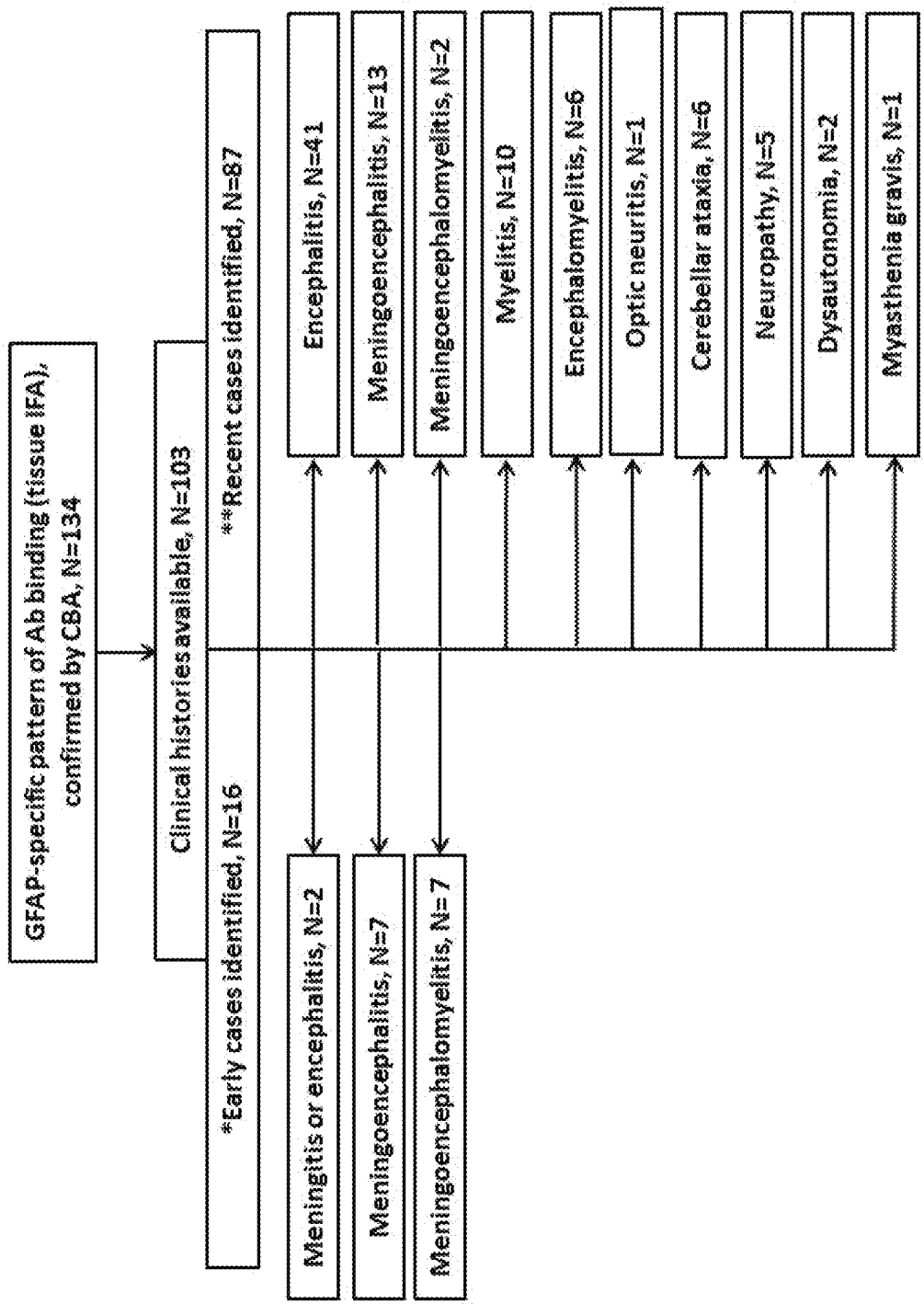
FIG. 1. Clinical presentations of 103 GFAP-specific IgG-positive human patients identified in screening for neural-specific autoantibodies by the mouse tissue-based immunofluorescence assay (IFA) described herein. (Ab is abbreviation for autoantibody). *GFAP specificity confirmed by cell-based recombinant antigen assay.

This document provides methods and materials for identifying and/or treating autoimmune GFAP astrocytopathy. For example, this document provides methods and materials for identifying a human as having an autoimmune GFAP astrocytopathy based on the presence of GFAP-specific IgG within a biological sample obtained from the human (e.g., a serum sample or a CSF sample).

Any appropriate method can be used to determine if a human has GFAP-specific IgG. For example, a biological sample obtained from a human can be assessed for the presence of GFAP-specific IgG using immunohistochemical methods such as tissue-based immunohistochemistry, transfected cell-based immunofluorescence assays, immunofluorescence assays using cultured glial cells or cell lines, Western blot analyses, or ELISA assays. In some cases, a human's CSF sample can be diluted (e.g., diluted 1:1 in phosphate-buffered saline), or a human's serum sample can be diluted (e.g., diluted 1:120) and pre-absorbed with liver powder. The samples can be assessed using tissue-based immunofluorescence assay (e.g., 4 cryosections of adult mouse cerebellum-midbrain-cerebral cortex-hippocampus, kidney and stomach; permeabilized with 1% 3-[(3-cholamidopropyl) dimethylammonio]-1-propanesulfonate, 4 minutes, then fixed in 10% formalin, 4 minutes, and blocked in normal goat serum, 10% in phosphate-buffered saline, 1 hour). After washing in phosphate-buffered saline, and applying a fluorochrome-conjugated IgG specific for human IgG for 35 minutes and washing again, the sample can be examined by fluorescence microscopy, looking for the immunostaining pattern typical of GFAP. GFAP specificity is confirmed by cell-based assay, using, for example, fixed, permeabilized GFAPα-transfected cells (e.g., HEK293) as substrate. In some cases, a Western blot assay can be performed on a lysate of GFAPα-transfected cells. Any appropriate biological sample can be obtained from a human undergoing clinical evaluation for symptoms that raise suspicion for autoimmune meningoencephalomyelitis and used to determine if GFAP-specific IgG is present. For example, a sample of serum, plasma, or CSF can be obtained from the human (or a sample of umbilical cord blood from a newborn or amniotic fluid from a pregnant woman with autoimmune GFAP meningoencephalomyelitis can be obtained) to determine if that human (or child) has GFAP-specific IgG present.

Once a human is determined to have GFAP-specific IgG, the human can be classified as having an autoimmune GFAP astrocytopathy, provided the clinical context is appropriate (namely meningoencephalomyelitis spectrum). For example, a human with meningitis, encephalitis, myelitis, or all three (meningoencephalomyelitis) and detectable GFAP-specific IgG within a serum or CSF sample can be classified as having an autoimmune GFAP astrocytopathy. In some cases, a human can be classified as having an autoimmune GFAP astrocytopathy based on the presence of GFAP-specific IgG in addition to one or more symptoms such as headache, rapid cognitive decline, psychiatric symptoms, seizures, weakness, tremor, and blurred vision.

In some cases, a human determined to have an autoimmune GFAP astrocytopathy as described herein can be treated using the methods and materials provided herein. For example, a human classified as having an autoimmune GFAP astrocytopathy can be administered or instructed to self-administer immunosuppressant therapy. In other words, a human identified as having an autoimmune GFAP astrocytopathy as described herein can be administered (or instructed to self-administer) an immunosuppressant therapy to treat the autoimmune GFAP astrocytopathy. Examples of immunosuppressant therapy that can be used to treat autoimmune GFAP astrocytopathy include, without limitation, corticosteroid therapy (e.g., high dose corticosteroid therapy where the dose is greater than 1.0 mg of methylprednisolone/kg), mycophenolate mofetil, azathioprine as a steroid-sparing drug for long term therapy, or a combination thereof.

This document also provides methods and materials for identifying humans having autoimmune GFAP astrocytopathy as being likely to have underlying cancer (e.g., an adenocarcinoma or teratoma). For example, this document provides methods and materials for identifying a human having an autoimmune GFAP astrocytopathy as being likely to have an underlying teratoma based on the presence of NMDA-R-specific IgG, AQP4-specific IgG, or both NMDA-R-specific IgG and AQP4-specific IgG within a biological sample (e.g., a CSF sample or serum sample) obtained from that human.

As described herein, about thirty-eight percent of humans with GFAP-specific IgG have an underlying cancer (e.g., adenocarcinoma or teratoma). The likelihood of cancer (e.g., teratoma) is greatest if GFAP-specific IgG is accompanied by NMDA-R-specific IgG or AQP4-specific IgG, or both. The human's cerebrospinal fluid can be characteristically inflammatory (white blood cells, predominantly lymphocytic, may number in the hundreds; protein level and IgG index may be elevated).

Any appropriate method can be used to determine if a human has NMDA-R-specific IgG and/or AQP4-specific IgG. For example, a biological sample obtained from a human can be assessed for the presence of NMDA-R-specific IgG and/or AQP4-specific IgG using immunological methods such as tissue-based immunofluorescence assays or antigen-specific transfected cell-based assays, which are either live or fixed. In some cases, a cell-based assay using indicator cells (e.g., HEK293) transfected with the NR1 subunit of NMDA receptor can be used to determine the presence of NMDA-R-specific IgG within a human. In some cases, AQP4-specific IgG can be detected using a flow cytometric assay with indicator cells (e.g. HEK293) transfected with the M1 isoform or M23 isoform of AQP4 as antigen. In some cases, observer-scored cell-based immunofluorescence assays using either M1 or M23 AQP4 isoform as antigen can be used.

Any appropriate biological sample can be obtained from a human to be assessed and used to determine if NMDA-R-specific IgG and/or AQP4-specific IgG is present. For example, serum samples, CSF samples, and plasma samples can be obtained from a human to be assessed and used to determine if that human has NMDA-R-specific IgG and/or AQP4-specific IgG present.

Once a human having an autoimmune GFAP astrocytopathy is determined to have NMDA-R-specific IgG and/or AQP4-specific IgG, the human can be classified as being likely to have an underlying cancer. Examples of cancers that the human can be classified as being likely to have include, without limitation, adenocarcinoma (e.g., an adenocarcinoma of endometrium, stomach, esophagus, or kidney), glioma, head and neck squamous cell carcinoma, multiple myeloma, pleomorphic parotid adenoma, teratoma (e.g., ovarian teratoma), and carcinoid cancers. In some cases, a human can be classified as being likely to have an underlying cancer (e.g., teratoma) based on the additional presence of NMDA-R-specific IgG and/or AQP4-specific IgG plus one or more symptoms such as headache, confusion, weakness, psychiatric disturbance, blurred vision, and tremor. For example, a human with GFAP-specific IgG autoantibodies and one or more elements of meningitis, encephalitis, or myelitis plus detectable NMDA-R-specific IgG and/or AQP4-specific IgG within a serum, plasma, or CSF sample can be classified as being likely to have an underlying cancer.

In some cases, a human having an autoimmune GFAP astrocytopathy and determined to be likely to have an underlying cancer as described herein can be treated using the methods and materials provided herein. For example, a human having an autoimmune GFAP astrocytopathy and identified as being likely to have an underlying cancer (e.g., a teratoma) based, at least in part, on the presence of NMDA-R-specific IgG and/or AQP4-specific IgG can be treated for that cancer or can be evaluated at regular future intervals if initial cancer evaluation is non-revealing.

This document also provides kits for identifying humans with autoimmune GFAP astrocytopathy. For example, a kit for identifying humans with autoimmune GFAP astrocytopathy can include a source of GFAP antigen and anti-human IgG antibodies. In some cases, the GFAP antigen can be a human GFAP polypeptide, a mouse GFAP polypeptide, a rat GFAP polypeptide, a dog GFAP polypeptide, a cat GFAP polypeptide, a goat GFAP polypeptide, a horse GFAP polypeptide, a bovine GFAP polypeptide, a hamster GFAP polypeptide, a rabbit GFAP polypeptide, a monkey GFAP polypeptide, or a fragment of any such GFAP polypeptides. In some cases, the GFAP antigen can be a full-length human GFAP or a polypeptide fragment of GFAP (e.g., a fragment of amino acid residues 1 to 338 of human GFAP). An example of human GFAP is set forth in GenBank Accession No. NM_002055 (GI No. 334688841) or NP_002046 (GI No. 4503979). The anti-human IgG antibodies can be fluorescently labeled. For example, an anti-IgG antibody can have a fluorescent moiety covalently attached to it. In some cases, such a kit can include a human GFAP-specific IgG as a positive control. If another labeled probe (e.g., staph protein A or protein G) is used to detect a human's IgG, the positive control anti-GFAP IgG can be antiserum from an immunized rabbit or other species, rather than from a human.

This document also provides kits for identifying autoimmune GFAP astrocytopathy humans who have an underlying cancer or humans with underlying cancer without symptoms of neurological autoimmunity. For example, such a kit can include a source of NMDA-R antigen and/or a source of AQP4 antigen, in combination with an anti-IgG antibody. In some cases, the NMDA-R antigen can be a human NMDA-R polypeptide, a mouse NMDA-R polypeptide, a rat NMDA-R polypeptide, a dog NMDA-R polypeptide, a cat NMDA-R polypeptide, a goat NMDA-R polypeptide, a horse NMDA-R polypeptide, a bovine NMDA-R polypeptide, a hamster NMDA-R polypeptide, a rabbit NMDA-R polypeptide, a monkey NMDA-R polypeptide, or a fragment of any such NMDA-R polypeptides. In some cases, the NMDA-R antigen can be full-length human NMDA-R or a polypeptide fragment of NMDA-R (e.g., a fragment of amino acid residues 26 to 382 of human NMDA-R) or a NR1 subunit. An example of human NMDA-R is set forth in GenBank Accession No. NM_007327 (GI No. 297374806) or NP_015566 (GI No. 11038637). In some cases, the AQP4 antigen can be a human AQP4 polypeptide, a mouse AQP4 polypeptide, a rat AQP4 polypeptide, a dog AQP4 polypeptide, a cat AQP4 polypeptide, a goat AQP4 polypeptide, a horse AQP4 polypeptide, a bovine AQP4 polypeptide, a hamster AQP4 polypeptide, a rabbit AQP4 polypeptide, a monkey AQP4 polypeptide, or a fragment of any such AQP4 polypeptides. In some cases, the AQP4 antigen can be full-length human AQP4 or a polypeptide fragment of AQP4 (e.g., a fragment of amino acid residues 23 to 323 of human AQP4). An example of human AQP4 is set forth in GenBank Accession No. NM_001317384.1 (GI No. 959071841) or NP_001304313 (GI No. 959071842). The anti-IgG antibody for detecting human IgG binding to a kit antigen can be an anti-human IgG antibody that is labeled (e.g., fluorescently labeled). For example, an anti-IgG antibody can have a fluorescent moiety covalently attached to it. In some cases, such a kit can include NMDA-R-specific IgG and/or AQP4-specific IgG as positive controls. If another labeled probe (e.g., staph protein A or protein G) is used to detect a human's IgG, the positive control anti-GFAP IgG could be antiserum from a rabbit or another species.

This document also provides kits for determining whether or not a human has an autoimmune GFAP astrocytopathy accompanied by an underlying cancer (e.g., a teratoma). For example, a kit for determining whether or not a human has an autoimmune GFAP astrocytopathy accompanied by an underlying cancer can include (a) a GFAP antigen, (b) an NMDA-R antigen and/or an AQP4 antigen, and (c) an anti-human IgG antibody.

In some cases, a kit for determining whether or not a human has an autoimmune GFAP astrocytopathy accompanied by an underlying cancer can include a GFAP antigen, an NMDA-R antigen, an AQP4 antigen, and an anti-human IgG antibody. In some cases, the GFAP antigen can be full-length human GFAP or a polypeptide fragment of GFAP as described herein. In some cases, the NMDA-R antigen can be full-length human NMDA-R or a polypeptide fragment of NMDA-R as described herein. In some cases, the NMDA-R antigen can be the NR1 subunit (e.g., incorporating the N368/G369 region of the amino terminal domain of human NMDA-R). In some cases, the AQP4 antigen can be full-length human AQP4 or a polypeptide fragment of AQP4 as described herein. In some cases, the anti-IgG antibodies can be anti-human IgG antibodies. The anti-IgG antibodies can be labeled (e.g., fluorescently labeled). For example, an anti-IgG antibody can have a fluorescent moiety covalently attached to it. In some cases, such a kit can include GFAP-specific IgG, NMDA-R-specific IgG and/or AQP4-specific IgG as positive controls. If another labeled probe (e.g., staph protein A or protein G) is used to detect a human's IgG, the positive control anti-GFAP IgG could be antiserum from a rabbit or other species rather than a human autoantibody.

The invention will be further described in the following examples, which do not limit the scope of the invention described in the claims.

EXAMPLES

Example 1—Autoimmune GFAP Astrocytopathy: A Novel Meningoencephalomyelitis

Study Population

Sera used to characterize the GFAP autoantibody were representative of seropositive cases (about 134 cases) identified in blinded service laboratory evaluation of >100,000 patients suspected clinically to have an autoimmune neurological disorder. Control specimens included 455 sera (mouse tissue-based immunofluorescence assay: 173 healthy Olmsted County residents; GFAP-specific cell-based assays (CBA): 135 healthy Mayo Clinic Biobank subjects (100 adult; 35 pediatric), 20 patients with multiple sclerosis, 57 AQP4-IgG-seropositive neuromyelitis optica spectrum disorder, 35 SLE or Sjogren syndrome, 35 hypergammaglobulinemia) and 49 CSFs (CBA: 26 normal pressure hydrocephalus (adults) and 23 miscellaneous disorders (children)). This example describes the autoantibody characteristics and antigen identity, and clinical synopsis of neurologic, oncologic, and radiologic findings, companion autoantibodies and immunotherapy responses for the 16 initially-identified seropositive patients.

Controls specimens for tissue-based immunofluorescence assay (IFA) (459 total) were: a) 393 serums total: from 1) 288 healthy adult donors (173 resident of Olmsted County, Minnesota and 115 from the Mayo Clinic Biobank), 2) 35 patients with hypergammaglobulinemia, 3) 35 patients with systemic lupus erythematous (SLE), 4) 35 pediatric patients with miscellaneous non-autoimmune neurological disorders, and b) 66 CSF specimens from: 1) 13 adult patients with normal pressure hydrocephalus and 2) 53 patients with miscellaneous non-autoimmune neurological disorders (21 adult, 32 pediatric). Control specimens for transfected cell-based assays (CBAs) (281 total) were: a) 205 serums from: 1) 100 Mayo Clinic Biobank healthy donors, 2) 35 patients with hypergammaglobulinemia, 3) 35 patients with systemic lupus erythematous, and 4) 35 pediatric patients with miscellaneous non-autoimmune neurological disorders, and b) 76 CSF specimens from: 1) 26 adult patients with normal pressure hydrocephalus, and 2) 50 pediatric patients with miscellaneous non-autoimmune neurological disorders.

Immunohistochemical Assays

Screening employed 4 μm cryosections of adult mouse cerebellum-midbrain-cerebral-cortex-hippocampus, kidney, and stomach (Meeusen et al., *Ann. Neurol.*, 71(3):417-26 (2012)). Research studies employed juvenile rat spinal cord sections. After permeabilization (1% CHAPS, 4 minutes), fixation (10% formalin, 4 minutes), and blocking (normal goat or swine serum, 10% in phosphate buffered saline (PBS), 1 hour), patient serum (bovine liver powder-pre-absorbed, 1:120 dilution) or CSF (non-absorbed, 50% dilution) and commercial polyclonal IgG antibodies (rabbit, pan-GFAP (1:5000, Z 0334, Dako), GFAP-δ (1:500, PA1-06702, Pierce Biotechnology), GFAP-ε (1:100, ab28926, ab93251, Abcam, USA); goat, GFAP-α-specific (C-19) (1:100, sc-6170, Santa Cruz Biotechnology, Inc.)) were applied. After 40 minutes, and PBS-wash, secondary antibody (35 minutes; species-specific anti-IgG, FITC- or TRITC-conjugated; Southern Biotechnology Associates, Inc.) were applied. Glass coverslips were applied to washed sections using PROLONG™ Gold anti-fade mounting medium (containing DAPI; Molecular Probes). Fluorescence images were captured using Axiovision software (Zeiss, Thornwood, NY, USA). Specimens yielding positive results were titrated (doubling dilutions) to determine the autoantibody detection endpoint. For dual-staining, patient serum and rabbit monoclonal intermediate filament-specific IgG (e.g., vimentin (ab92547, Abcam, USA) or desmin (ab32362, Abcam, USA)) (1:200) and secondary antibodies (1:100; TRITC-conjugated goat anti-rabbit-IgG and donkey anti-human IgG, Jackson Immuno) were applied. Confocal images were captured using Zeiss LSM710 microscope (63× or 40× water immersion lens).

Cultured Cells

HEK293 cell-lines stably transfected with plasmids encoding respectively GFAP *Homo sapiens* transcript variant 1 (RG 204548; pCMV6-AC-GFAP-α-GFP) and variant 2 (RG225707, pCMV6-AC-GFAP-δ/ε-GFP; OriGene, Inc.) were selected in geneticin (0.8 g/mL, GIBCO BRL). Human glioblastoma multiforme cells (GBM, serially xenografted in athymic nude mice) were provided by Dr. Jann Sarkaria (Mayo Clinic; Higgins et al., *Oncotarget.*, 4(5):792-801 (2013)).

Cell-Based Immunofluorescence Assays

Cells, fixed (4% paraformaldehyde, 15 minutes) and permeabilized (0.2% TRITON™ X-100, a detergent, 10 minutes), were held overnight at 4° C. with patient serum (1:10 dilution), CSF (undiluted), rabbit pan-GFAP-IgG (1:5000), rabbit GFAP-ε-IgG (1:100) or goat GFAP-α-IgG (C-19; 1:20). After PBS-wash and incubation with secondary antibodies (1:200), images were captured by confocal microscopy (Zeiss LSM710; 63× or 40× water immersion lens).

Antigen Identification

Adult rat spinal cord and GBM cells were extracted in 0.15 M NaCl, 0.01 M NaPO$_4$, 2 mM EDTA, pH 7.2, containing 1% TRITON™ X-100 (a detergent), 0.1% SDS, and protease inhibitors (Complete™, Roche 11697498001). Lysate clarified by centrifugation (400 g, 10 minutes), was sequentially centrifuged 30 minutes (4000 g, 8000 g, 100000 g and 300000 g). Reduced/denatured supernatants and pellets of each fraction were separated by gel electrophoresis (10% polyacrylamide), transferred to nitrocellulose, and probed with patient serum or CSF (BioRad molecular weight standards (161-0374)). To determine molecular identity, the most informative fraction was solubilized in 2-dimension electrophoresis sample buffer, loaded onto 13 cm Immobiline™ DryStrip (pH 4-7; GE Healthcare, Sweden) and applied a final voltage of 3500 V for 20 hours. Second-dimension electrophoresis was performed on 10% polyacrylamide gel. After nitrocellulose membrane transfer (0.45 μm CAS #9004-70-0, Bio-Rad, USA), separated proteins were visualized by silver staining and autoradiography (western blot). Peptides were identified (MASCOT search algorithm) in excised immunoreactive spots analyzed by in-gel digest/tandem mass spectrometry.

Western Blot

Stably-transfected and non-transfected HEK293 cell lysates (in 50 mM Tris-HCl, pH 7.5, 150 mM NaCl, and 2% TRITON™ X-100—a detergent) were clarified by centrifugation (1000 rpm, 5 minutes), electrophoresed in 10% polyacrylamide gel, transferred electrophoretically to nitrocellulose membrane, blocked in buffer (20 mM Tris, pH 7.6, 137 mM sodium chloride, 0.1% TWEEN®-20—a nonionic surfactant and an emulsifier) containing 10% powdered milk, and then probed 1 hour with IgG specific for GFAP-α (1:50), GFAP-ε/δ (1:100), pan-GFAP (1:10,000), or actin (1:2000), patient serum (1:100), CSF (1:10), or healthy control serum and CSF. After three 5-minute washes (20 mM Tris, pH 7.6, 137 mM NaCl, 0.1% TWEEN®-20—a nonionic surfactant and an emulsifier), blots were incubated for 30 minutes with horseradish peroxidase-conjugated goat anti-rabbit IgG, swine anti-goat IgG, or goat anti-human IgG (1:2000). After washing, bound IgG was detected autoradiographically by enhanced chemiluminescence (SuperSignal West Pico Luminol/Enhancer; Thermo Scientific product #34080).

Results

Astrocytic Autoantibody Characterization

Figure 2:
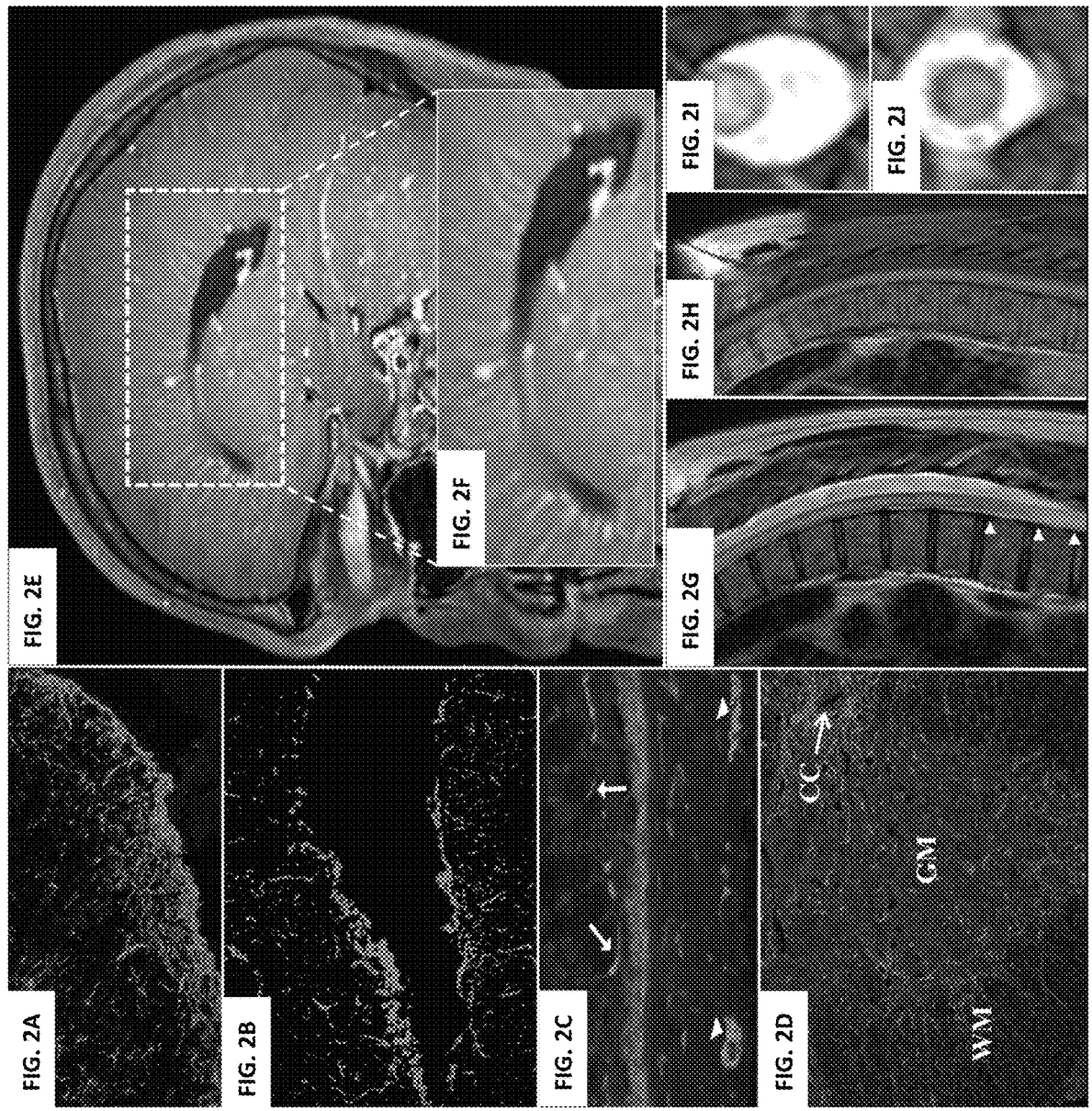
FIGS. 2A-2J. Immunofluorescence pattern of human patient IgG bound to rodent CNS tissue sections in part resembles brain and spinal cord MR imaging patterns of patients with autoimmune GFAP meningoencephalomyelitis.

IgG in all 16 patients intensely stained cytoplasmic filaments in histologically-restricted astrocyte populations. None of 173 Olmsted County healthy control sera yielded this pattern. Apart from 87 subsequently-identified seropositive patients (FIG. 1), this pattern was not yielded by any serum or CSF specimen among more than 100,000 patients with miscellaneous neurological disorders tested by service tissue-based immunofluorescence assay. Immunostaining in mouse brain was confined to pia, subpia, and midbrain foci (FIG. 2A), periventricular region (FIG. 2B) and rostral migratory stream (not shown). Enteric ganglia and nerves with mucosa-penetrating filaments were prominent immunoreactive elements in the periphery (FIG. 2C); renal nerve elements were non-immunoreactive. In spinal cord, immunoreactive filaments were prominent around the central canal and in gray matter, radiating to pia (FIG. 2D).

Neurological Correlations

Table 1 summarizes the 16 patients' clinical and laboratory findings. Evaluations were not conducted uniformly, but no alternative diagnoses were established (infectious, granulomatous, inflammatory demyelinating, lymphomatous, carcinomatous or vasculitic). Median age at neurological symptom onset was 42 years (range, 21-73); there was no sex predominance. The common clinical presentation was disabling corticosteroid-responsive meningoencephalitis or encephalitis, with or without myelitis. Fourteen patients had meningeal and encephalitic symptoms; seven additionally had myelitic symptoms; eight had vision changes; and two had isolated meningeal or encephalitic symptoms. Subacute headache was the most common symptom (12 patients).

Prominent clinical findings were optic disc edema without increased intracranial pressure (optic papillitis, 7 patients), myelopathy, tremor, ataxia, progressive cognitive impairment, autonomic instability and psychiatric disturbance. No patient had seizures. Continuing retrospective history review for subsequent GFAP-IgG-seropositive patients confirmed association with CNS inflammation (to date 92% of 103 cases; FIG. 1). A minority (8%) had a peripheral nervous system disorder (neuropathy, dysautonomia or myasthenia gravis).

TABLE 1

Demographic, Clinical, Imaging, Serum and CSF Findings in 16 GFAP-IgG-positive Patients

| Sex/age at onset | Diagnosis | Monophasic/relapsing | Presenting symptoms | MRI findings | CSF protein/white cells/unique oligoclonal bands (OCB)/IgG Index | Coexisting autoimmune disease/autoantibodies (value) | Cancer detected | Immunotherapy response | GFAP-IgG titer/isoform Serum | CSF |
|---|---|---|---|---|---|---|---|---|---|---|
| 1. F/31 | Meningo-encephalitis | Monophasic | Headache, weight loss, cognitive change, hemiparesis, vomiting, abnormal movements | Brain: Diffuse leptomeningeal T2 hyperintensities & post-gadolinium enhancement | 94 mg/dL/144/μL (99% lym)/OCB unknown/index 1.08 | No | No | No Immunotherapy | 49,1520/ α + ε | Not available |
| 2. F/43 | Meningo-encephalitis | Unknown | Altered mental status, hallucinations | Brain: Diffuse gyral & leptomeningeal enhancement | 80 mg/dL/50/μL (80% lym)/OCB & index unknown | No | No | Unknown | 61,440/ α + ε | Not available |
| 3. F/27 | Meningo-encephalitis | Monophasic | Headache, hallucinations, obtundation | Not available | Protein unknown/500/μL (80% lym)/OCB & index unknown | No | | Improved | 15,360/ α | 128/ α + ε |
| 4. M/73 | Encephalitis* | Relapsing | Subacute onset lethargy, weight loss, confusion, imbalance, depression. Viral encephalitis suspected. Subsequent painless bilateral vision loss | Brain: Diffuse T2 hyperintensitie, periventricular white matter | Protein unknown/4/μL (93% lym)/OCB & index unknown/ | Arthritis/VGCC-P/Q (0.04 nM); thyroglobulin[36] | Prostate adenocarcinoma | No Immunotherapy | 15,360/ α | Not available |
| 5. F/21 | Meningo-encephalitis* | Relapsing | Headache, behavioral changes, delirium, paranoia, progressive imbalance, vision loss | Brain: Cerebellar leptomeningeal T2 hyperintensities & post-gadolinium enhancement. | 113 mg/dL/308/μL (96% lym)/OCB unknown/index Normal | NMDAR IgG (CSF pos) | No | Improved | 3,840/ α + ε | 256/ Not available |
| 6. F/65 | Meningo-encephalomyelitis | Relapsing | Headache, dysphagia, dysarthria, tremor, meningismus, weight loss, limb weakness | Not available | Elevated/Elevated/OCB & index Unknown | Diabetes mellitus | PET: hypermetabolic uptake left hepatic lobe | Improved | 3,840/ Not available | Not available |
| 7. F/29 | Meningo-encephalomyelitis* | Relapsing | Headaches, photophobia, reduced taste/olfaction. Vision loss, tremor, left lateral thigh numb | Brain & upper C cord: Diffuse perivascular & leptomeningeal enhancement, some nodular | 192 mg/dL/77/μL (95% lym)/OCB 8/index 1.29 | Graves thyroiditis/GAD65 (4.16 nM); TPO[36] | Parotid pleomorphic adenoma | Improved | 1,920/ negative | 512/ α + ε |

TABLE 1-continued

Demographic, Clinical, Imaging, Serum and CSF Findings in 16 GFAP-IgG-positive Patients

| Sex/age at onset | Diagnosis | Mono-phasic/relapsing | Presenting symptoms | MRI findings | CSF protein/white cells/unique oligoclonal bands (OCB)/IgG Index | Coexisting autoimmune disease/autoanti-bodies (value) | Cancer detected | Immuno-therapy response | GFAP-IgG titer/isoform Serum | CSF |
|---|---|---|---|---|---|---|---|---|---|---|
| 8. M/53 | Encephalo-myelitis | Monophasic | Headache, tremor, jerking limbs, palpitations, flushing, pre-syncopal sensation, blurred vision (Due to Left Cranial nerve VI palsy). Subsequent tremulousness, imbalance, urine retention, weight loss, diplopia, unstable gait, cognitive decline, night mares | Brain: Diffuse radial periventricular T2 hyperintensities & post-gadolinium enhancement (perivascular). Cord: T2 abnormalities | 205 mg/dL/90/μL (99% lym)/OCB 6/Index Normal | interstitial pneumonia; nonspecific myositis/VGCC-P/Q (0.03 nM) | No | Improved | 1,920/α | 64/α + ε |
| 9. F/43 | Encephalitis | Relapsing | Headache, vomiting, weight loss, movement disorder, constipation, postural light-headedness, dry mouth | Brain: Diffuse T2 hyperintensities left occipital & parietal lobes. Perivascular enhancement, linear & nodular. Cord: extensive T2 hyperintensities, cervical & thoracic | 169 mg/dL/148/μL (90% lym)/OCB 5/Index Unknown | GAD65 (0.04 nM); TPO | No | Improved | 1,920/α + ε | 256/α + ε |
| 10. M/32 | Encephalo-myelitis* | Relapsing | Headache, subacute blurred vision, polyuria/polydipsia, weight loss. Viral encephalitis suspected. Fatigue, intractable insomnia, depression. Progressed to gait disorder, urine retention, constipation, emotional lability, poor memory, confusion | Brain: Diffuse hemispheric & pontine radial periventricular T2 hyperintensities, perivascular post-gad enhancement. Cord: extensive T2 hyperintensities cervical and thoracic with parenchymal enhancement | 79 mg/dL/58 μL (88% lym)/OCB 2/index 1.23 | Diabetes-type 1/ GAD65 (0.24 nM) | No | Improved | 1920/Negative | Not avail-able |
| 11. M/37 | Meningo-encephalo-myelitis* | Relapsing | Headache, vision changes, tremor, imbalance, lightheaded; cognitive changes, weakness, sensory loss, erectile dysfunction | Brain & cord: Diffuse brain and upper cervical T2 abnormalities. Perivascular brain enhancement, leptomeningeal cord enhancement | 112 mg/dL/185/μL (97% lym)/OCB 5/index unknown | No | No | Improved | 480/α + ε | Not avail-able |

TABLE 1-continued

Demographic, Clinical, Imaging, Serum and CSF Findings in 16 GFAP-IgG-positive Patients

| Sex/age at onset | Diagnosis | Monophasic/relapsing | Presenting symptoms | MRI findings | CSF protein/white cells/unique oligoclonal bands (OCB)/IgG Index | Coexisting autoimmune disease/autoantibodies (value) | Cancer detected | Immunotherapy response | GFAP-IgG titer/isoform Serum | CSF |
|---|---|---|---|---|---|---|---|---|---|---|
| 12. M/51 | Meningoencephalomyelitis* | Relapsing | Headache, subacute tremor, weight loss, Gastrointestinal symptoms, fatigue, blurred vision, malaise, emotional lability, hyperactive startle, cognitive change | Brain & cord: Diffuse brain and lower thoracic cord T2 abnormalities, perivascular brain enhancement, leptomeningeal cord enhancement | 101 mg/dL/121/L (98% lym)/OCB None/index normal | No | Colonic carcinoid | Improved | 120/Negative | 256/α + ε |
| 13. M/40 | Meningoencephalitis | Unknown | Headache; no other details | Not available | Not available | No | Metastatic melanoma | Unknown | Not available | 256/α + ε |
| 14. F/25 | Meningoencephalomyelitis | Monophasic | Flu-like illness, myelitis, coma; no other details | Not available | Not available | NMDAR-IgG (CSF pos) | Teratoma | Unknown | Not available | 8192/α + ε |
| 15. M/21 | Chronic meningitis* | Monophasic | Headache, weight loss, vision changes, nausea, aural fluttering sound, abdominal pain, orthostatic dizziness | Brain: Small areas of non-enhancing T2 hyperintensity in white matter and caudate head | 64 mg/dL/26/μL (97% lym)/OCB 6/Index 0.90 | Diabetes-Type 1; alopecia universalis/TPO[36]; SCL70[36]; ANA[36]; cold agglutinin[36]; polyclonal gammopathy | No | Improved | Not available | 256/α + ε |
| 16. M/61 | Meningoencephalitis* | Monophasic | Headache, fever, confusion | Small areas of T2 hyperintensity hemispheric white matter; enhancement (<1 cm) right temporal lobe | 149 mg/dL/190/μL (98% lym)/OCB normal/index normal | No | Multiple myeloma | Improved | Not available | 512/α + ε |

*Bilateral optic papillitis found on examination.

Abbreviations: ANA = antinuclear antibody; CSF = cerebrospinal fluid; F = female; GAD65 = glutamic acid decarboxylase, 65 kDa isoform; lym = lymphocytes; M = male; nM = nmol/L; NMDAR = n-methyl-D-aspartate receptor; OCBs = oligoclonal bands; pos = positive; SCL-70 = 70 kDa immunoreactive fragment extractable from topisomerase-1 antigen; TPO = thyroperoxidase; VGCC-P/Q = neuronal voltage-gated calcium channel, P/Q-type.

Normal values: Serum: GAD65 antibody and VGCC-P/Q antibody, ≤0.02 nmol/L. CSF: protein ≤35 mg/dL; white cells, ≤5/μL; unique oligoclonal bands, <4; IgG index, <0.85.

Figure 3:
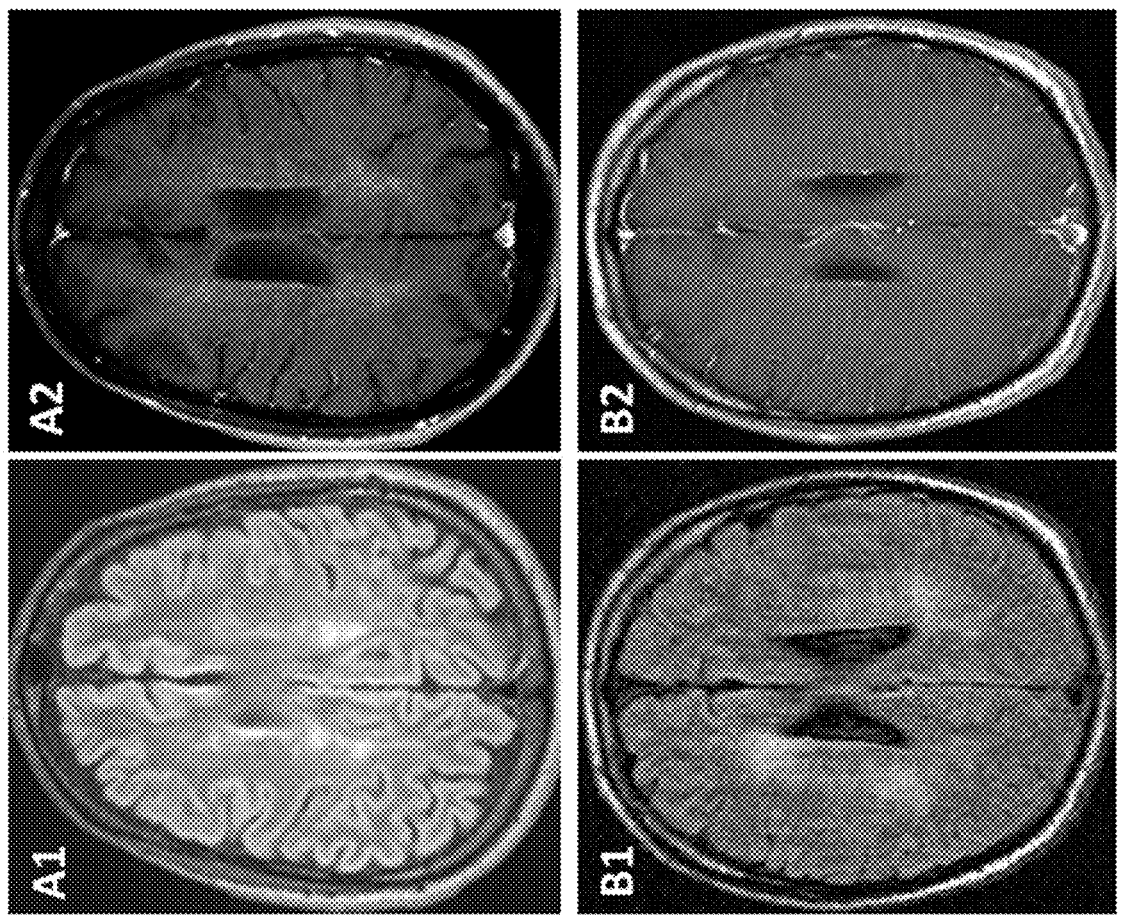
FIG. 3. Additional brain magnetic resonance images from two human patients with GFAP astrocytopathy. Patient 10 (A): Note punctate periventricular T2 signal abnormality on fluid attenuated inversion recovery (A1) and T1 post gadolinium enhancement (A2); this patient's spinal cord image is shown in FIG. 1, G-I. Patient 12 (B): Note hazy periventricular T2 FLAIR signal abnormality (B1) with radial pattern of gadolinium enhancement (B2).

Cranial/spinal magnetic resonance images (MRI, available for 12/16 patients) revealed diffuse T2 abnormalities in periventricular white matter (9/12; Table 1); six cases had prominent linear perivascular enhancement oriented radially to the ventricles, and four had leptomeningeal enhancement. Spinal MRI showed longitudinally-extensive T2 hyperintensity (5/7 patients with myelopathy) or was normal (two patients, myelitic symptoms). FIGS. 2E-2I demonstrate, for two patients, resemblances of MRI enhancement patterns (cranial and spinal, respectively) to the immunohistochemical staining patterns of patient IgG on meningeal and parenchymal elements in rodent brain and spinal cord (FIGS. 2B, 2D, and 3). CSF was inflammatory (13/14 patients with available data): 4-500 leukocytes/μL (median 121; >80% lymphocytes [normal≤μL]; elevated protein (64-205 mg/dL; median 112; normal≤35 mg/dL), supernumerary oligoclonal bands (5 patients) and elevated IgG index (3 patients). CSF opening pressure was elevated (298 mm $H_2O$) in one of eight recorded cases.

Available clinical, radiological and CSF findings classified the 16 patients as: meningoencephalitis, 6; meningoencephalomyelitis, 5; encephalomyelitis, 2; encephalitis, 2 and meningitis, 1 (Table 1).

Coexisting Disorders

Seven patients had additional evidence of autoimmunity (Table 1): glutamic acid decarboxylase 65-kDa isoform antibody (3 patients; 1 had type 1 diabetes mellitus), thyroperoxidase-IgG (3 patients; 1 had Graves thyroiditis), P/Q-type voltage-gated calcium channel antibody (2 patients; 1 had interstitial pneumonitis and myositis; the other had prostate adenocarcinoma), NMDA-R IgG (CSF, 2 patients; 1 paired serum specimen also positive; both had meningoencephalitis, 1 had teratoma; neither had classic autoimmune NMDAR encephalitis) and anti-nuclear antibody (1 patient). Miscellaneous immunopathies included polyclonal hypergammaglobulinemia and IgA deficiency.

Six patients had documented cancer, past or current (7 neoplasms; 5 after neurological symptom onset and 2 before): two adenocarcinomas (prostate; gastroesophageal coexisting with myeloma), metastatic melanoma, colonic carcinoid, parotid pleomorphic adenoma ("mixed tumor") and teratoma. The median interval from neurological symptom onset to cancer diagnosis was 3 months (range, −24 to +36).

Eleven patients (of 13 with treatment information) received immunotherapy; all responded favorably to initial intravenous high-dose corticosteroid, but seven relapsed during dose tapering. No relapse occurred in 6 who received long-term immunosuppression (mycophenolate, 5; azathioprine, 1).

Autoantigen Identification

Immunohistochemistry

Figure 4:
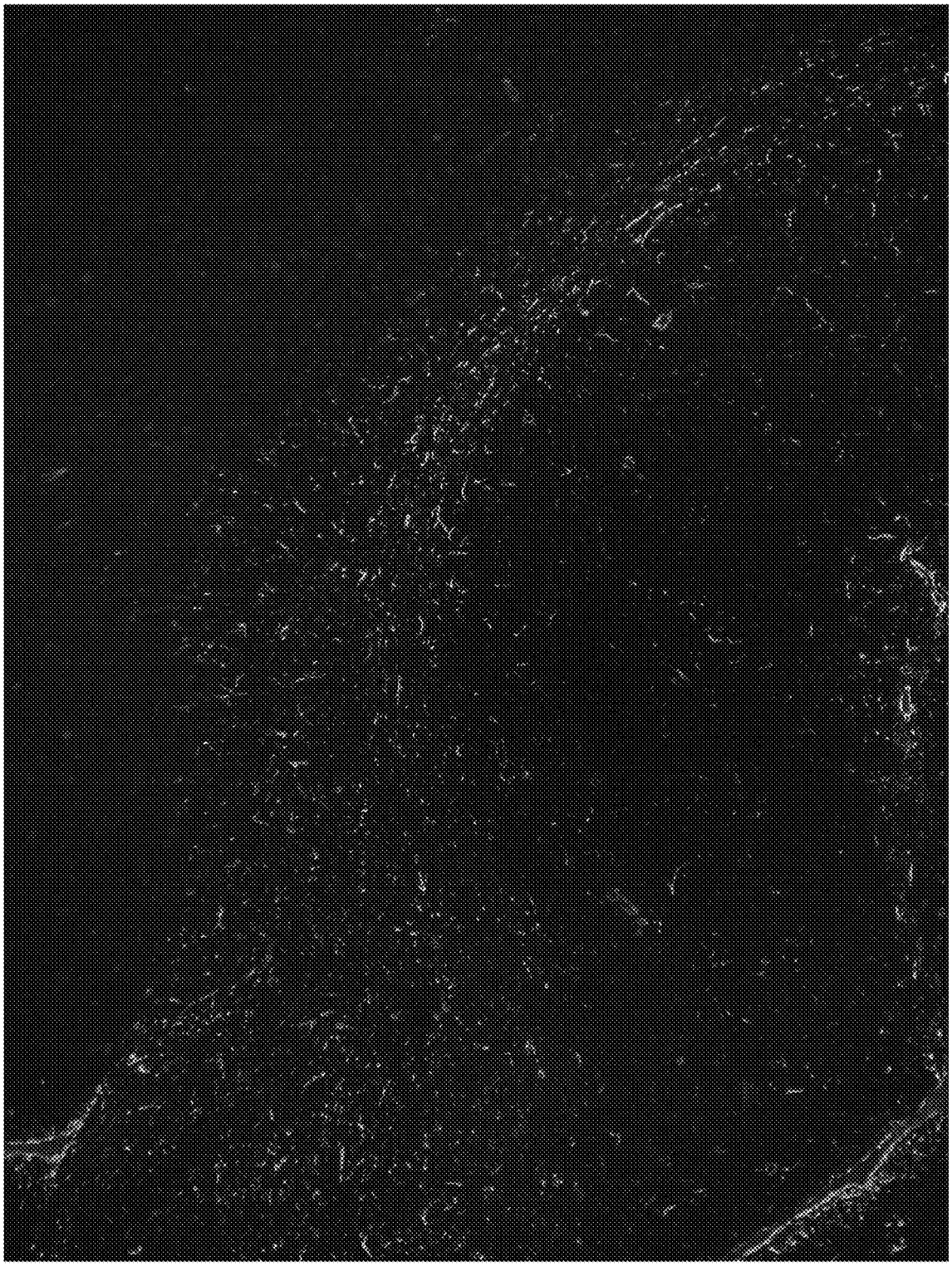
FIG. 4. Rostral migratory stream. IgG in serum of human patient with autoimmune GFAP astrocytopathy binds prominently to filamentous elements in astro-neuronal progenitor cells of the rostral migratory stream in indirect immunofluorescence image of adult mouse brain tissue. Ependyma and periventricular astrocytes also are immunoreactive (top and bottom, left). Original magnification 20×.

Intermediate filament antigens were investigated. Desmin immunoreactivity co-localized with patient IgG in pia, subpia (FIG. 4); divergence in gut smooth muscle (patient IgG non-reactive) lessened the likelihood of desmin being antigen. Patient IgG co-localized partially with CNS vimentin immunoreactivity, but divergent cellular staining reduced the likelihood of vimentin being antigen.

Figures 5A, 5B, 5C, 5D, 5E, 5F:
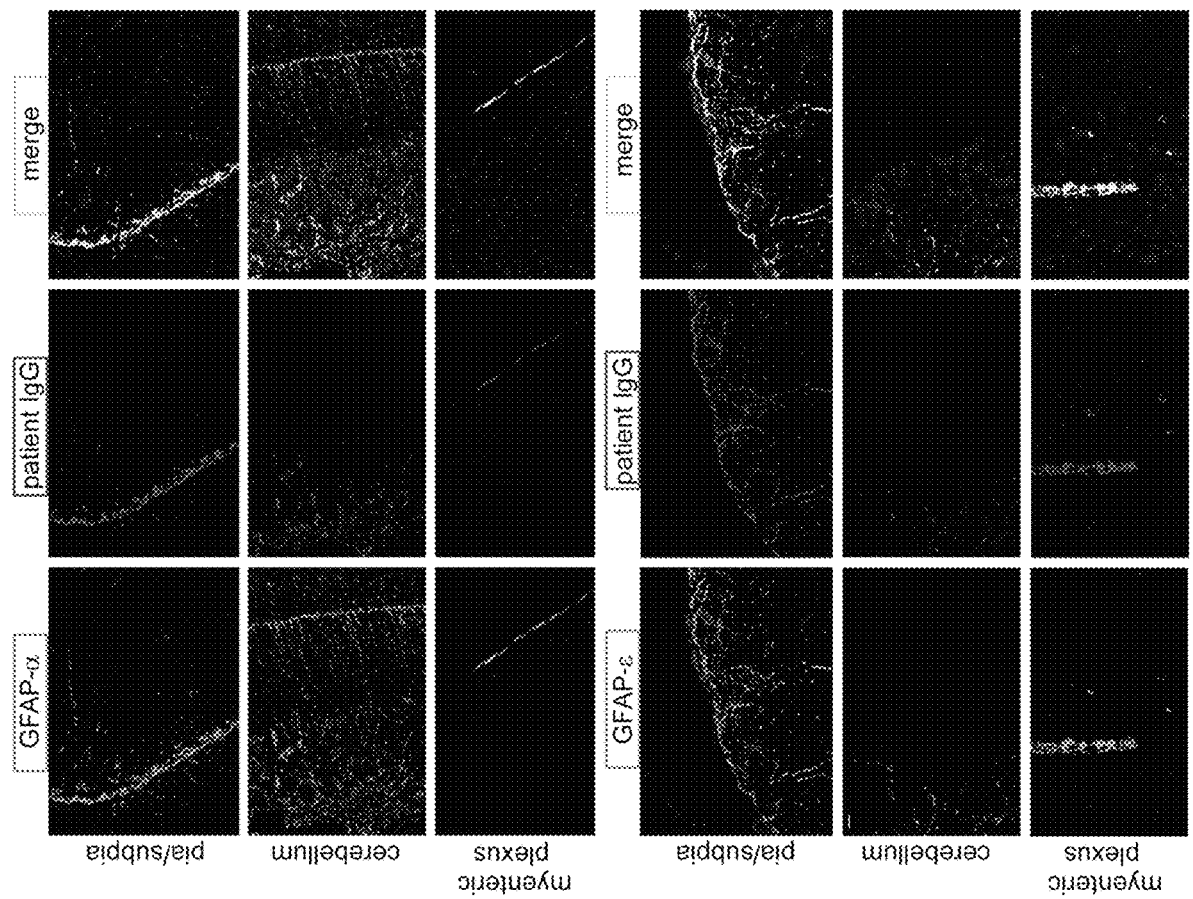
FIGS. 5A-5F. Dual immunostaining of mouse tissues with commercial IgGs specific for GFAP intermediate filament isoforms and human patient IgG.
Figure 8:
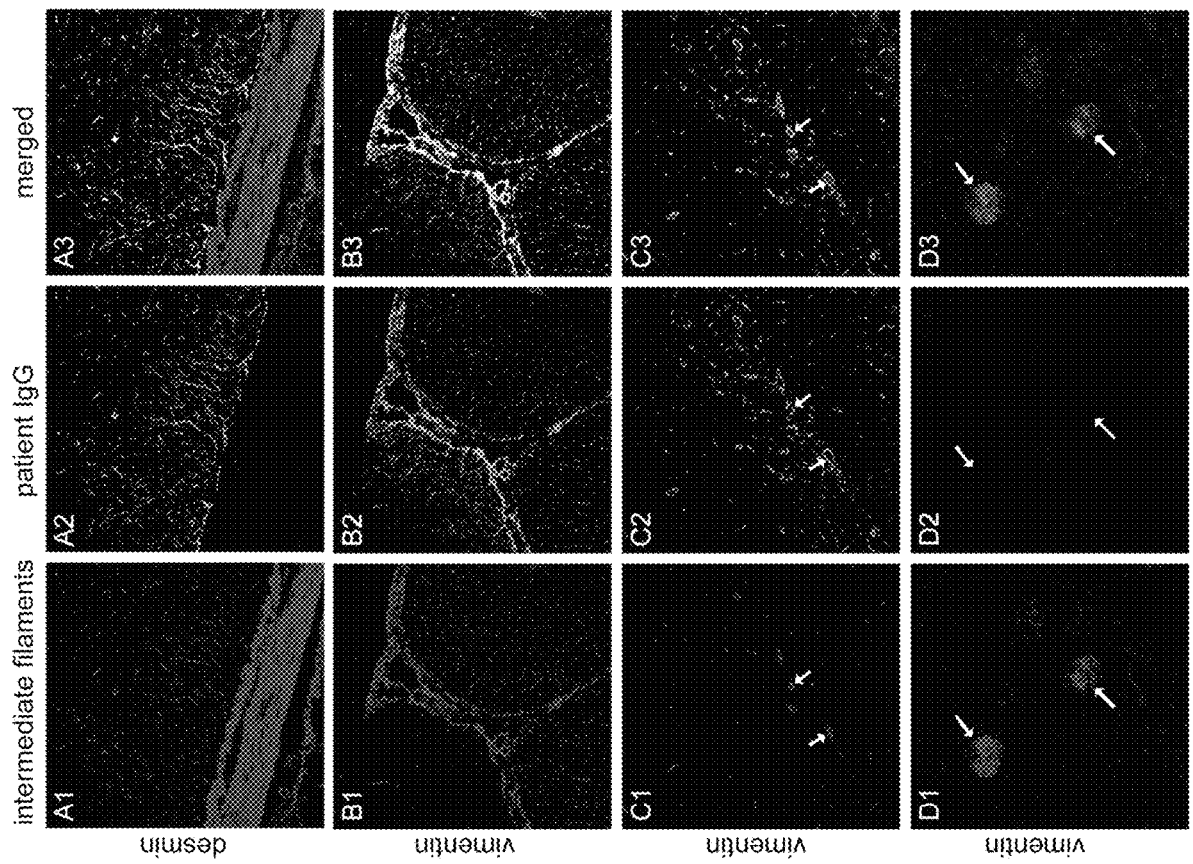
FIG. 8. Dual binding of human patient IgG and desmin-specific IgG or vimentin-specific IgG. Immunofluorescence staining of mouse tissues by commercial intermediate filament IgGs (red) and patient IgG (green). A. Desmin-IgG co-localized with patient IgG (×10) in astrocytes of midbrain pia and subpia (yellow in merged figure). Patient IgG did not colocalize with desmin-IgG in smooth muscle fibers of gut (lower one third of A; mucosa at bottom left). B. Vimentin-IgG and patient IgG immunoreactivities (×10) diverged in some CNS parenchymal regions but coincided in pia/subpia (yellow in merged figure). C. Endothelium in hippocampus (arrows, ×20) and renal glomeruli (arrows, D×20) were positive only for vimentin. DNA is blue (DAPI stain in merged panels).

Patient IgG partially co-localized with the GFAP intermediate filament α-isoform in pial, subpial (FIG. 5A), and subventricular astrocytes, but not in GFAP-α-positive-ependyma. Processes in myenteric plexus presumptive glia were prominently dual-reactive (FIG. 5B). Bergmann radial glial processes bound GFAP-α-specific-IgG more intensely than patient IgG (FIG. 5C). GFAP-δ/ε-specific-IgG co-localized with patient IgG in all examined neural tissues: pia and subpia (FIG. 5D), subventricular zones, cerebellar cortex (FIG. 5E) and myenteric plexus (FIG. 5F). Like patient IgG, GFAP-δ/ε-IgG bound to Bergmann glial filaments far less intensely than GFAP-α-IgG. Thus, patient IgG binding was relatively restricted to GFAP-δ/ε-expressing astrocytes.

Immunochemical Characterization of Autoantigen

Western blot probing of rat spinal cord proteins with four patients' IgGs revealed a common immunoreactive band, ~50 kDa; control human IgGs were non-reactive (FIG. 6A). Antigenicity was further demonstrated in the 50 kDa protein by re-applying to tissue sections patient IgG acid-eluted from a replicate band (i.e., not subjected to western probing; FIG. 6B).

A GBM xenograft tumor cell line was identified as enriched in the human glial antigen by immunofluorescence screening of candidate glial lines with patient IgG (FIG. 6C). Commercial pan-GFAP-reactive IgG, GFAP-δ/ε-specific IgG and patient IgG, but not control human IgG, yielded filamentous cytoplasmic staining. By western blotting, patient IgG revealed antigenicity in a GBM cytoskeletal protein (8000 g insoluble fraction; FIG. 6D). Mass spectrometry analysis of common immunoreactive spots to which two individual patients' IgGs bound (FIG. 6E) yielded partial sequences common to N-terminal and rod domains of all GFAP isoforms. Consistent with previously reported 2-dimensional electrophoretic analysis of human brain GFAP, 10 patient IgGs bound to multiple polypeptides (interpreted to be different modification and degradation products of GFAP).

Reactivity with Isolated GFAP Isoforms

To determine whether patient IgG bound selectively to GFAP-δ/ε, GFAP-α or to isoform-common epitopes, HEK293 cells were transfected with expression plasmids encoding individual human GFAP isoforms tagged with green fluorescent protein. IgG binding analyzed on permeabilized cells (immunofluorescence) and lysates (western blot) yielded concordant results. Commercial pan-GFAP-reactive IgG bound to both GFAP-α and GFAP-ε (FIG. 7A); commercial GFAP-α-IgG or GFAP-δ/ε-IgG bound exclusively to the corresponding isoform (FIGS. 7B and 7C). IgG in only 5 of 282 control human sera tested (1.8%) bound to GFAP isoform-transfected cells (FIG. 7D): 3/135 healthy, 1/70 miscellaneous immunopathies, 1/57 NMOSD but 0/20 MS. Importantly, none of those 5 bound to mouse tissue sections. Serum or CSF was available from 15/16 patients for isoform testing. IgG bound to GFAP-α-cells (8/11 sera, and 9/9 CSFs; illustrative examples, FIGS. 7E and 7F). Serum IgG was dual-reactive (5/11), solely GFAP-α-reactive (3/11) or non-reactive (3/11). IgG in all 9 CSF specimens was dual-reactive (FIG. 7F). No serum or CSF was GFAP-ε-mono-reactive. No IgG bound to non-transfected cells. None of 49 control CSFs reacted with isolated GFAP.

These results demonstrate that GFAP auto-antibodies can be used to identify an autoimmune meningoencephalomyelitis that is immunotherapy-responsive. One third of cases have serological evidence of autoimmune endocrinopathy (some clinically evident); more than one third are paraneoplastic. The clinical presentation is generally subacute. Headache is prominent. Common symptoms and signs are encephalitic, papillitis without increased intracranial pressure, and myelopathy. The astrocytic cytoplasmic intermediate filament protein, GFAP, is the autoantigen.

Example 2—Autoimmune GFAP Astrocytopathy

Patients

All included patients (102) had (a) serum, CSF, or both revealing the characteristic GFAP-IgG pattern of staining by an indirect immunofluorescence assay (IFA), in which a composite of mouse brain, kidney, and gut was utilized (see Example 1), (b) GFAP-specificity confirmed by cell-based assays (CBAs), and (c) clinical data available. All patients were evaluated serologically; clinical evaluations occurred at Mayo Clinic (detailed, 38, Table 2), or elsewhere (limited data, 64).

Review of a 20-year clinical laboratory archive revealed 874 patients in whom the characteristic GFAP-IgG tissue IFA pattern had been detected in serum, CSF, or both (approximately 44 cases per year). At this time, about one patient per week is identified in the laboratory (compared to about three per week with NMDA-R encephalitis).

TABLE 2

Clinical, testing, treatment and outcome data for the 38 Mayo Clinic patients

| Patient No. Sex/Age | Clinical syndrome | MRI brain | MRI spine | CSF WCC*/Pro/OCs/IgG SR/IgG Ind | Serum IFA titer/CBA GFAP isoform | CSF IFA titer/CBA GFAP isoform | Treatment response Acute | Chronic steroid-sparing | mRS/follow-up (mo) |
|---|---|---|---|---|---|---|---|---|---|
| 1. F/26 | Encephalitis** | T/Ra/Se/Bs/Ce | NA | 219/49/N/N/N | 240/$\alpha + \varepsilon + \kappa$ | 4/$\alpha + \varepsilon$ | S | R | 2/36 |
| 2. M/72 | Ataxia, peripheral neuropathy | NA | NA | N/N/N/N/N | 7680/$\alpha + \varepsilon$ | NA | NA | NA | 3/0 |
| 3. F/56 | Meningo-encephalitis | Bs | N | N/43/N/N/N | 30720/$\alpha + \varepsilon$ | NA | NA | NA | 1/3 |
| 4. M/61 | Meningo-encephalitis | T/Ra/Se/Bs | N | 123/149/N/31.8/N | Neg/$\alpha$ | 512/$\alpha + \varepsilon$ | NA | NA | 6/52 |
| 5. M/64¶ | Meningencephalomyelitis | T/Ra/Bs | LETM | 121/101/N/N/N | 120/N | 256/$\alpha + \varepsilon$ | S | M, A | 1/144 |
| 6. M/32¶ | Encephalo-myelitis | T/Ra | LETM | 58/79/N/39.06/1.23 | 120/N | 64/$\alpha + \varepsilon$ | S | A | 0/120 |
| 7. M/53¶ | Encephalitis | T/Ra/Bs | LETM | 90/205/6/N/N | 1920/$\alpha$ | NA | S/IVIg/P | M | 2/72 |
| 8. M/39¶ | Meningo-encephalitis | T/Ra/Bs | LETM | 32/48/N/N/N | 480/$\alpha + \varepsilon$ | NA | S | M | 1/24 |
| 9. F/29 | Meningo-encephalitis | T/Ra/Ce | NA | 77/192/8/80/1.29 | 1920/N | 512/$\alpha + \varepsilon$ | S | M | 1/29 |
| 10. F/52 | NMO*** | T | N | N/N/N/N/N | 1920/$\alpha + \varepsilon + \kappa$ | Pos/$\alpha + \varepsilon$ | No response (S) | A | 2/84 |
| 11. M/21 | Meningitis | Ra | NA | 26/64/6/18.1/0.90 | NA | 256/$\alpha + \varepsilon + \kappa$ | NA | NA | 1/2 |
| 12. F/74 | Dementia | N | NA | NA | 3840/$\alpha + \varepsilon + \kappa$ | NA | NA | NA | 6/60 |
| 13. M/58 | Encephalopathy | T (Choroid plexus glioma) | NA | NA | 122880/$\alpha + \varepsilon$ | NA | NA | NA | 6/36 |
| 14. M/53 | Cranial neuropathy | N | N | NA | 960/$\alpha + \varepsilon$ | NA | NA | NA | 0/12 |
| 15. M/73 | Encephalitis, optic neuritis | N | NA | NA | 15360/$\alpha + \varepsilon + \kappa$ | Pos/NA | NA | NA | 2/24 |
| 16. F/50 | Peripheral neuropathy | N | NA | NA | 7680/$\alpha + \varepsilon$ | NA | NA | NA | 1/72 |
| 17. F/31 | Meningo-encephalitis | T/Ra/Se/L | N | 144/94/N/28.1/1.08 | 491, 520/$\alpha + \varepsilon + \kappa$ | NA | NA | NA | 6/1 |
| 18. F/38 | Meningitis** | N | N | N/N/NA/NA/NA | 1920/$\alpha + \varepsilon$ | Neg | NA | NA | 2/3 |
| 19. F/43¶ | Meningoencephalomyelitis | T/Ra/Ep | LETM | 148/169/5/NA/NA | 1920/$\alpha + \varepsilon$ | 256/$\alpha + \varepsilon$ | S/IVIg | M | 0/36 |
| 20. F/24 | Encephalitis** | Ra/Bs/L | N | N/43/4/N | 1920/$\alpha + \varepsilon + \kappa$ | Pos | No response (S/IVIg/P) | No response (R/Cyc) | 4/24 |
| 21. F/19 | Encephalitis** | T/Ra/Bs/L | NA | 48/73/11/83/2.85 | 3840/$\alpha + \varepsilon$ | Pos/$\alpha + \varepsilon$ | S | NA | 1/36 |
| 22. F/22 | Encephalo-myelitis*** | T/Ra | LETM | 18/N/NA/NA/NA | 61440/$\alpha + \varepsilon + \kappa$ | NA | IVIg | NA | 0/6 |
| 23. F/62 | Myelitis | NA | NA | NA | 7680/$\alpha$ | NA | NA | NA | 3/0 |
| 24. M/75 | Myelitis | NA | N | NA | 7680/$\alpha + \varepsilon$ | NA | NA | NA | 2/0 |
| 25. M/51 | Myelitis | Ra | LETM | 17/72/13/39/1.8 | 480/$\alpha + \varepsilon$ | NA | NA | NA | 1/0 |
| 26. M/103 | Myasthenia gravis | NA | NA | NA | 960/$\alpha + \varepsilon + \kappa$ | NA | S | NA | 2/1 |
| 27. M/76 | Dysautonomia | N | NA | NA | 61440/$\alpha$ | NA | NA | NA | 3/0 |
| 28. F/55 | Cerebellar ataxia | NA | NA | NA | 61440/$\alpha + \varepsilon + \kappa$ | NA | NA | NA | 3/174 |
| 29. F/63 | Dysautonomia | NA | NA | NA | Pos/$\alpha$ | 64/$\alpha + \varepsilon + \kappa$ | NA | NA | 1/0 |
| 30. M/78 | Cerebellar ataxia | T/Se/L | NA | NA | Pos/$\alpha + \varepsilon + \kappa$ | Pos/NA | NA | NA | NA/72 |
| 31. F/45 | Optic neuritis, myelitis | T | STM | NA | 240/$\alpha$ | Pos/$\alpha$ | S | NA | 1/56 |
| 32. M/66 | Epilepsy | N | NA | NA | 1920/$\alpha$ | NA | NA | NA | 1/20 |
| 33. M/32 | Meningo-encephalitis*** | T/Se/L | NA | 22/N/N/N/N | Neg | 32/$\alpha + \varepsilon + \kappa$ | NA | NA | 1/8 |
| 34. M/31 | Encephalo-myelitis | T/Bs | N | N/44/N/N/0.86 | Neg | 32/$\alpha + \varepsilon + \kappa$ | S/IVIg/P | R | 4/31 |

TABLE 2-continued

Clinical, testing, treatment and outcome data for the 38 Mayo Clinic patients

| Patient No. Sex/ Age | Clinical syndrome | MRI brain | MRI spine | CSF WCC*/Pro/ OCs/IgG SR/IgG Ind | Serum IFA titer/CBA GFAP isoform | CSF IFA titer/CBA GFAP isoform | Treatment response Acute | Chronic steroid-sparing | mRS/ follow-up (mo) |
|---|---|---|---|---|---|---|---|---|---|
| 35. M/65 | Meningo-encephalitis | Ra/Se/Ep | N | 50/46/N/14.39/N | Neg | 128/α | S | NA | 1/8 |
| 36. M/69 | Meningo-encephalitis | T/Ra/Ep | N | 109/147/N/17.1/N | Neg | Pos/α + ε + κ | S | NA | 1/18 |
| 37. F/63 | Encephalitis | Ra | NA | 88/132/NA/NA/NA | Neg | 128/α | NA | NA | 3/2 |
| 38. M/55 | Limbic encephalitis | T (temporal astrocytoma) | NA | 66/67/N/N/N | Neg | 32/α | S/IVIg | NA | 3/15 |

A = azathioprine; Bs = brainstem enhancement; CBA = cell-based assay (indirect immunofluorescence); Ce = cerebellar enhancement; Cyc = cyclophosphamide; Ep = ependymal/subependymal; GFAP = glial fibrillary acidic protein; IFA = immunofluorescence assay (indirect, tissue-based); IVIg = intravenous immune globulin; IgG SR = IgG synthesis rate; IgG Ind = IgG index; L = leptomeningeal enhancement pattern; LETM = longitudinally extensive transverse myelitis (≥3 vertebral segments); mRS = modified rankin score; M = mycophenolate mofetil; N = normal; NA = not available; OCBs = oligoclonal bands (CSF-exclusive); P = plasma exchange; Pos = positive (insufficient specimen for titration); Pro = protein; Pt No = patient number; Ra = radial enhancement pattern; R = rituximab; S = corticosteroids; Se = serpentine pattern of enhancement; STM = short transverse myelitis; T = T2 signal abnormalities; WCC = white cell count.
¶Previously published in abstract form before discovery of GFAP-IgG[4]
*Elevated white cell counts were predominantly lymphocytic (median, 93%; range, 75-97%).
**NMDA-R-IgG coexisted in CSF
***AQP4-IgG coexisted in serum
Normal values
Tissue IFA: serum, <240; CSF, <2
CSF: protein ≤35 mg/dL; white cells, ≤5/μL; CSF-exclusive oligoclonal bands, <4; IgG synthesis rate, ≤12 mg/24 hours; IgG index, ≤0.85.

Controls

Control specimens for tissue IFA assay (459 total) were: a) 393 serums total: from 1) 288 healthy adult donors (173 resident of Olmsted County, Minnesota and 115 from the Mayo Clinic Biobank), 2) 35 patients with hypergammaglobulinemia, 3) 35 patients with systemic lupus erythematous (SLE), 4) 35 pediatric patients with miscellaneous non-autoimmune neurological disorders, and b) 66 CSF specimens from: 1) 13 adult patients with normal pressure hydrocephalus and 2) 53 patients with miscellaneous non-autoimmune neurological disorders (21 adult, 32 pediatric). Control specimens for CBAs (281 total) were: a) 205 serums from: 1) 100 Mayo Clinic Biobank healthy donors, 2) 35 patients with hypergammaglobulinemia, 3) 35 patients with systemic lupus erythematous, and 4) 35 pediatric patients with miscellaneous non-autoimmune neurological disorders, and b) 76 CSF specimens from: 1) 26 adult patients with normal pressure hydrocephalus, and 2) 50 pediatric patients with miscellaneous non-autoimmune neurological disorders.

Assays

Substrates for tissue-based IFA were 4 μm cryosections of adult mouse tissue composite (cerebellum, midbrain, cerebral cortex, striatum and hippocampus, kidney and stomach) and for CBA were stable clones of HEK293 cells transfected with plasmid from OriGene, Inc, encoding a single GFAP Homo sapiens transcript variant (variant 1: RG 204548, pCMV6-AC-GFAP-α-GF; variant 2: RG225707, pCMV6-AC-GFAP-δ/ε-GFP; or variant 3: RG234093, pCMV6-AC-GFAP-k-GFP). Cells were plated in 8 well poly-D-lysine coated chamber slides (Corning), fixed (4% paraformaldehyde, 15 minutes) and permeabilized (0.2% TRITON™ X-100—a detergent, 10 minutes). Normal goat serum (10%) was applied for 30 minutes to block non-specific IgG binding. After exposing to patient serum (1:200 dilution) or CSF (1:4) for 45 minutes at ambient temperature, cells were washed in PBS, then exposed to TRITC-conjugated goat anti-human IgG (1:200) for 45 minutes, washed in PBS and mounted in PROLONG™ Gold anti-fade reagent containing DAPI (Molecular Probes). Normal values for tissue IFA assays were: serum, <1:120; CSF, <1:2. Coexisting IgG neural autoantibodies were detected as described elsewhere (O'Toole et al., Neurology, 80(12):1133-44 (2013)).

Statistical Analysis

Summary statistics were reported as median (range, minimum-maximum) for continuous variables and as frequencies and percentages for categorical variables. Wilcoxon rank sum test or Fisher's exact test were used for comparison as appropriate. Analyses were performed using JMP 8.0 software (SAS®).

Results

Serological Results Among Controls

All control CSF specimens were negative by all assays. Two of 393 control serums were positive for GFAP-IgG by tissue IFA (0.5%, 1 healthy, and 1 with polyclonal hypergammaglobulinemia), but negative by CBAs. Three of 205 control serums were positive for GFAP auto-antibodies by CBA (1.5%, all healthy adults), but negative by tissue IFA. IgG in those sera bound to GFAPκ and GFAPε isoforms, 1 of which additionally bound to GFAPα.

Clinical Findings

The demographics, clinical, cerebrospinal fluid (CSF), and serologic findings of the 102 included patients were summarized in Table 3. The predominant clinical syndrome in 83 patients (81%) was one or more of meningitis, encephalitis, and myelitis (meningoencephalomyelitis, or limited forms of that, referred to from hereon as meningoencephalomyelitis). In CSF, 88% of patients had markedly elevated white cells (median number, 78/4; range, 13-550) and 83% had elevated protein (median, 80 mg/dL; range, 44-205), and 54% had elevated CSF-exclusive oligoclonal band numbers (Table 3). GFAP-IgG isoform specificities, detected in serum, CSF or both, by cell based assays were: α, all patients; ε, 76 (81%) and κ, 51 (54%, all of whom were also GFAPε-IgG positive) (Table 3 and FIG. 10).

TABLE 3

Clinical, laboratory, and serologic attributes of 102 GFAP-IgG positive cases

|  | Patients (%) | Median (range) |
|---|---|---|
| Demographics | | |
| Age at onset in years | | 44 (8-103) |
| Female sex | 55 (54%) | |
| Clinical Syndrome | | |
| Encephalitis* | 43 (42%) | |
| Meningoencephalitis | 13 (12.5%) | |
| Myelitis** | 11 (11%) | |
| Encephalomyelitis | 8 (8%) | |
| Meningitis | 5 (5%) | |
| Meningoenceph-alomyelitis | 3 (3%) | |
| Other[b] | 19 (18.5%) | |
| CSF findings | | |
| Elevated white cell count (>5/μL) | 45 of 51 (88%) | 78.5 (13-550)[c] |
| Elevated protein (>35 mg/dL) | 30 of 36 (83%) | 80 (44-205) |
| Hypoglycorrhachia (<40 mg/dL) | 4 of 22 (18%) | 37 (36-38) |
| CSF-exclusive oligo-clonal bands (≥4) | 13 of 24 (54%) | |
| Serological data | | |
| GFAP IFA positivity | 102 (100%) | |
| Serum IFA positive (Titer [end-dilution]) | 55 of 82 (67%) | 7680 (120-491520) |
| CSF IFA positive (Titer) | 64 of 68 (94%) | 128 (4-8192) |
| GFAPα CBA positive | 102 (100%) | |
| GFAPε CBA positive | 76 (81%) | |
| GFAPκ CBA positive | 51 (54%) | |

[b]Neuropathy, 8 (large fiber, 5; small fiber, 1; acute inflammatory demyelinating polyneuropathy, 1; cranial neuropathy, 1); ataxia, 5; encephalopathy in the context of brain tumors, 2; myasthenia gravis, 1; epilepsy, 1; dementia, 1; dysautonomia, 1.
[c]lymphocyte predominant, 94%; monocytic, 6%.
Abbreviations: CBA, cell based assay; CSF, cerebrospinal fluid; GFAP, glial fibrillary acidic protein; IF, immunofluorescence.
*3 of these had 1 each of opsoclonus-myoclonus syndrome, brainstem encephalitis, and optic neuritis.
**2 had a history of optic neuritis (one had neuromyelitis optica)

Neurological Findings

Thirty-eight patients evaluated at Mayo Clinic had detailed information available (Table 4). The most common clinical features encountered were encephalopathy, seizures, psychiatric symptoms, tremor, meningeal symptoms (including headache), myelopathic symptoms, blurred vision (due to optic disc edema, FIG. 11; panel D4). Eight patients (21%) had one or more coexisting autoimmune disorders: type 1 diabetes mellitus, 3; rheumatoid arthritis, 2; myasthenia gravis, 2 (1 had coexisting dysautonomia); alopecia, 1; Grave's disease, 1; and hypothyroidism, 1.

TABLE 4

Detailed clinical and neuroimaging characteristics of 38 Mayo Clinic GFAP-IgG positive cases

| Clinical features | Patients (%) |
|---|---|
| Subacute onset (<8 weeks) | 27 (71%) |
| CNS disorder | 33 (87%) |
| Encephalopathy | 21 of 37 (57%) |
| Tremor | 15 of 37 (41%) |
| Headache | 14 of 36 (39%) |
| Myelopathic symptoms/signs | 9 of 37 (24%) |
| Other meningeal symptoms/signs | 12 of 37 (32%) |
| Optic disc edema[a] | 12 of 37 (32%) |
| Ataxia | 10 of 35 (29%) |
| Psychiatric symptoms | 10 of 35 (29%) |
| Depression | 6 |
| Anxiety | 2 |
| Insomnia | 2 |
| Vivid dreams | 1 |
| Catatonia | 1 |
| Autonomic dysfunction | 8 of 34 (24%) |
| Orthostasis | 5 |
| GI motility disorders | 3 |
| Bladder dysfunction | 2 |
| Erectile dysfunction | 1 |
| Seizures | 7 of 37 (19%) |
| Eye movement disorder | 6 of 37 (16%) |
| Vomiting | 6 of 37 (16%) |
| Co-existing autoimmune disorder | 8 of 37 (22%) |
| Brain MRI findings | |
| Normal | 7 of 32 (22%) |
| Gadolinium enhancement | 21 of 32 (66%) |
| Abnormal T2-hyperintensity | 18 of 32 (56%) |
| Enhancement location | |
| Supratentorial | 20 of 32 (63%) |
| Infratentorial | 10 of 32 (31%) |
| Enhancement pattern | |
| Radial periventricular enhancement | 17 of 32 (53%) |
| Serpentine enhancement | 6 of 32 (19%) |
| Leptomeningeal enhancement | 7 of 32 (22%) |
| Subependymal enhancement | 3 of 32 (9%) |
| Spine MRI findings | |
| T2-hyperintensty (longitudinally extensive, 88%) | 8 of 19 (42%) |
| Gadolinium enhancement | 8 of 19 (42%) |
| Central cord enhancement | 4 of 19 (21%) |
| Acute treatment response and outcome | |
| Improved with corticosteroids | 14 of 16 (87.5%) |
| Improved with IVIg | 3 of 4 (75%) |
| Improved with PLEX | 1 of 2 (50%) |
| Duration of follow up (months) | 22 (0-174) |
| Median modified Rankin Score | 2 (0-6) |

[a]Normal CSF opening pressure in 6 of 8 cases suggested optic disc edema (papillitis); two had mildly elevated opening pressures (280 and 298 mm H20, respectively; normal ≤200).

Abbreviations: GFAP, glial fibrillary acidic protein; IVIg, intravenous immune globulin; PLEX, plasma exchange.

MRI Findings

Figure 11:
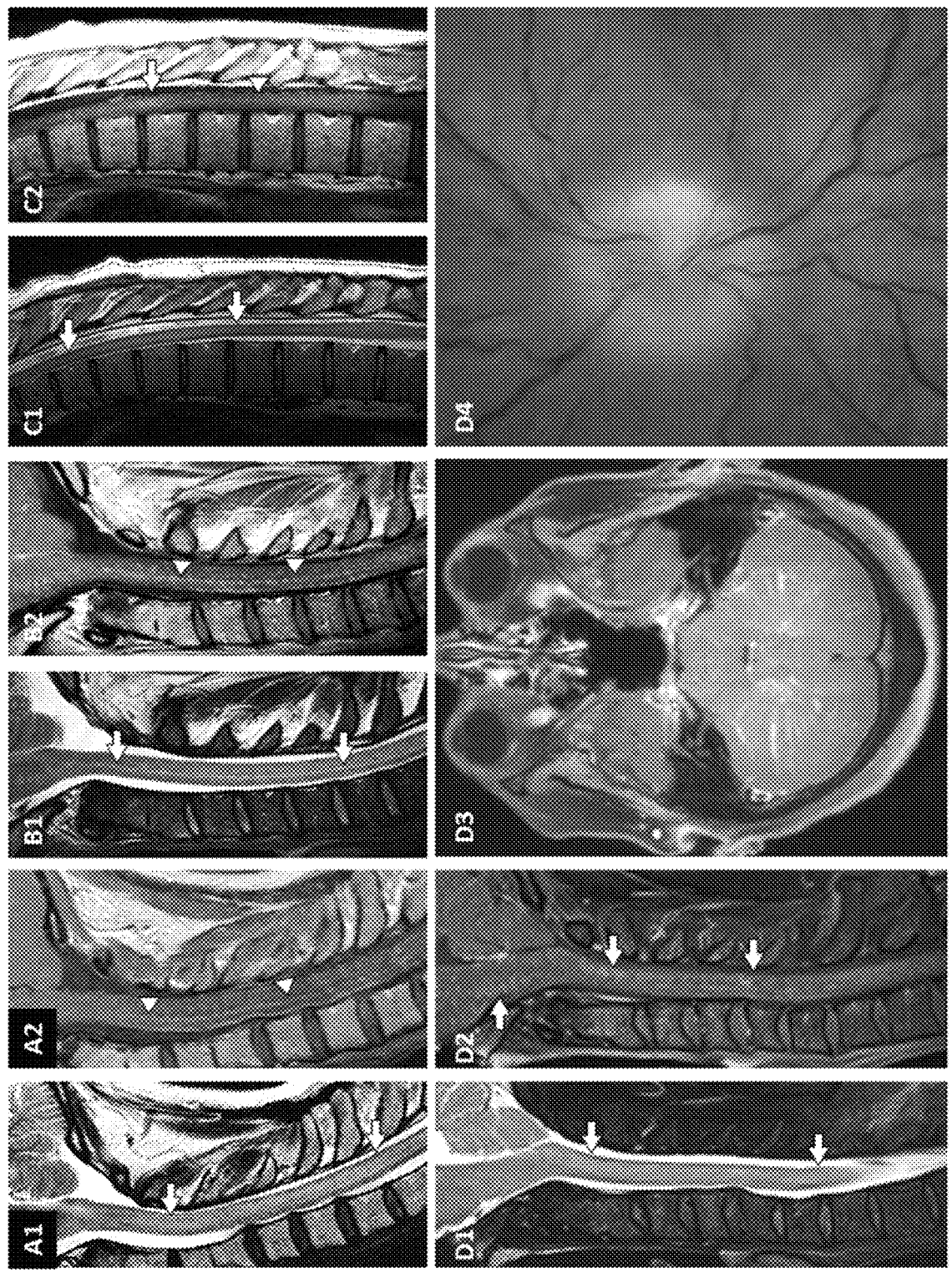
FIG. 11. Examples of infratentorial and spinal cord lesions in three human patients with autoimmune GFAP astrocytopathy, and fundoscopic appearance of optic disc edema in 1 patient. Cervical spine MRI sagittal sequences show longitudinally extensive T2-hyperintense lesions (A1, patient 19; B1, patient 8; C1, patient 6; arrows) accompanied by patchy enhancement (C2, arrow) and central canal enhancement (A2, B2, C2; arrowheads) on post-gadolinium sequences. MRI reveals faint longitudinally extensive T2-hyperintensity (D1, arrows) accompanied by patchy gadolinium enhancement in the medulla and spinal cord (D2, arrows) on sagittal cervical spine images and a radial pattern of cerebellar enhancement (D3) on axial post-gadolinium images brain images in patient 9; fundoscopy shows accompanying optic disc edema (D4).
Figure 12C:
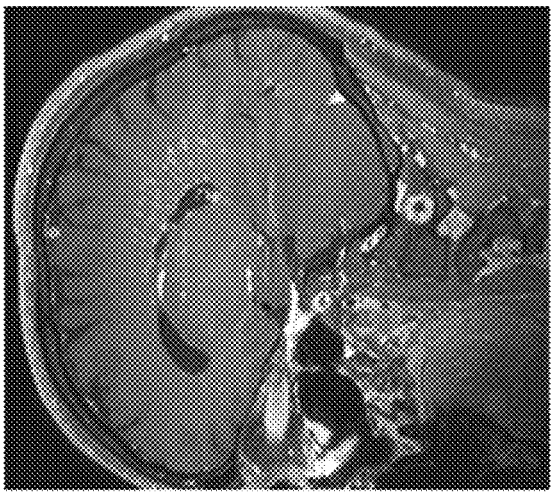
FIGS. 12A-12F. Examples of supratentorial gadolinium enhancement pattern in six human patients with autoimmune GFAP astrocytopathy. MRI T1-post gadolinium images demonstrate radial enhancement patterns, characteristically linear, extending outward from the ventricles on axial (FIG. 12A, patient 9.
Figure 12F:
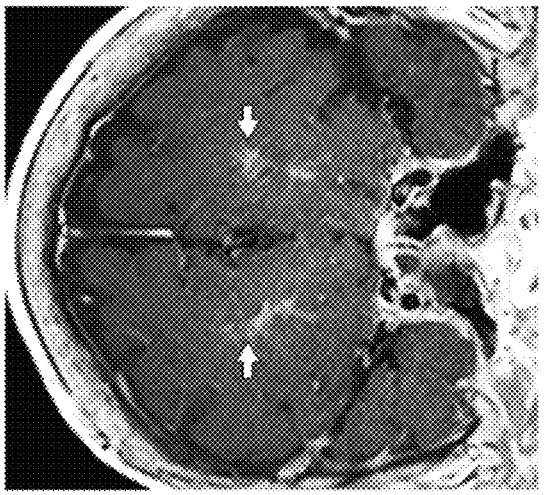
Figure 12B:
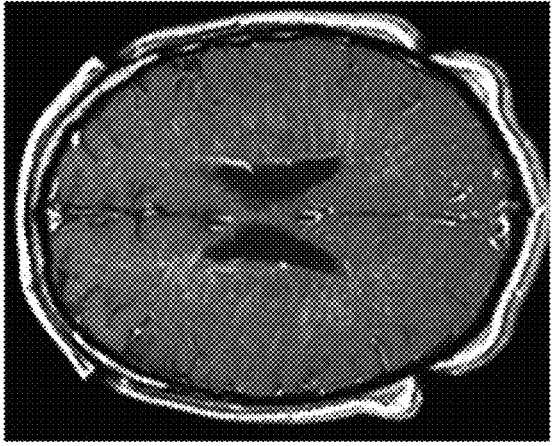
Figure 12E:
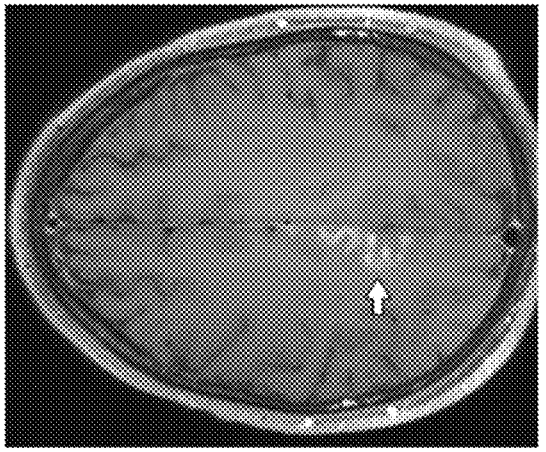
Figure 12A:
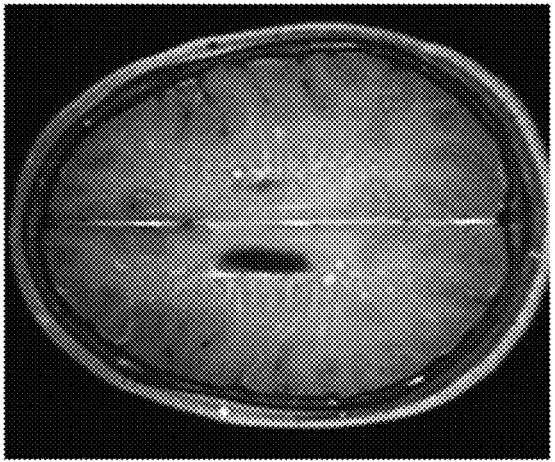
Figure 12D:
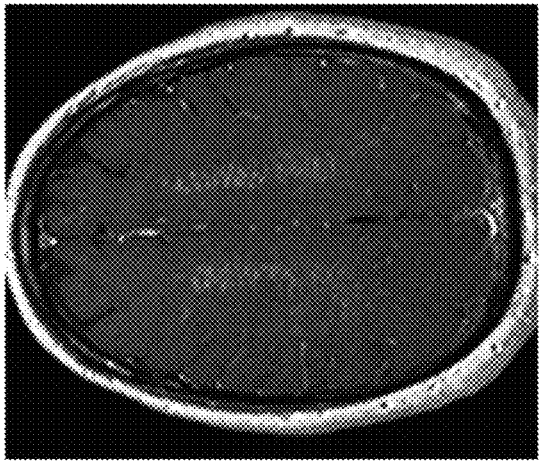
Figure 13:
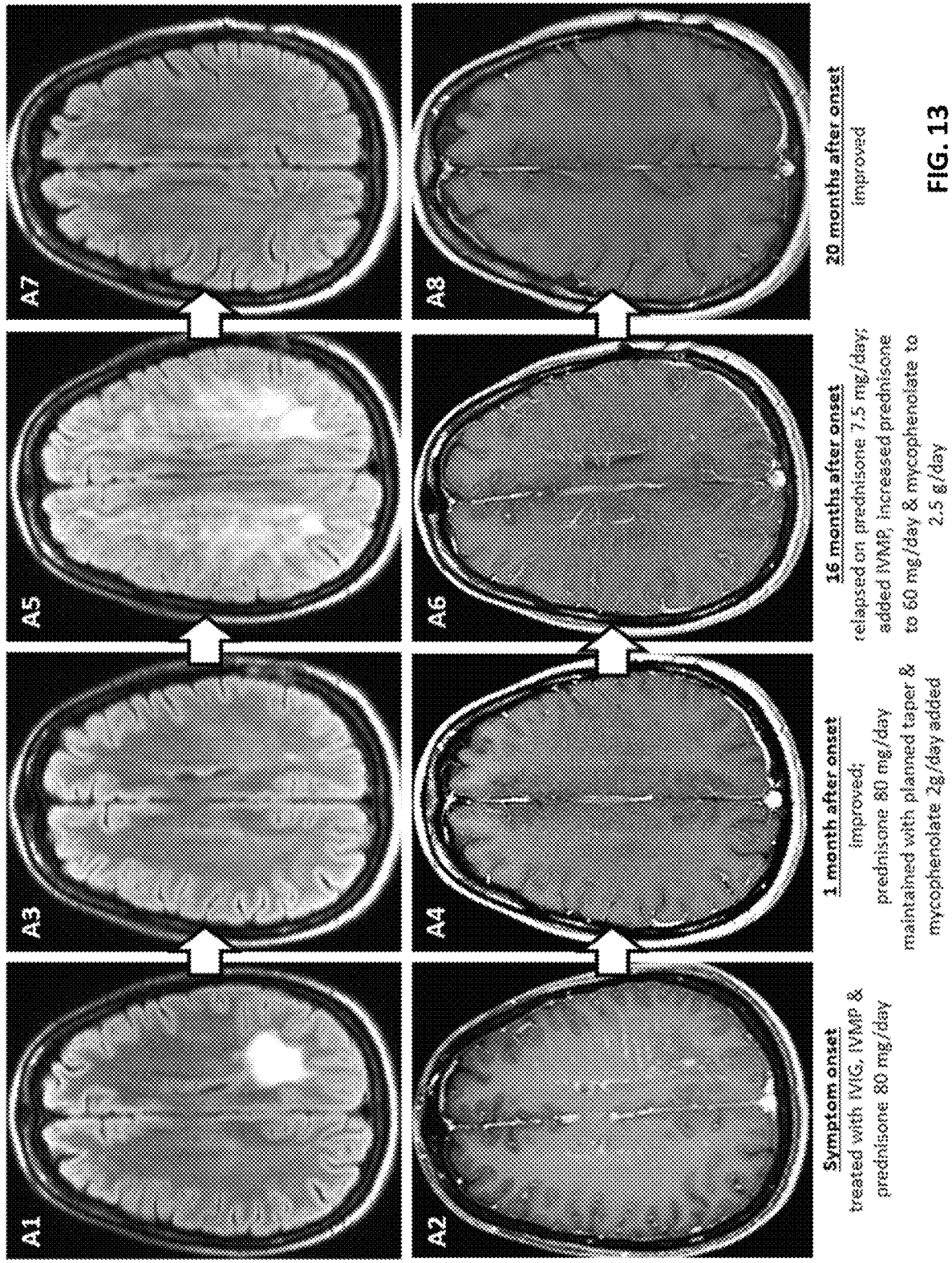
FIG. 13. Evolution of MRI abnormalities in patient 19 with relapsing autoimmune GFAP meningoencephalitis. Axial fluid inversion recovery (FLAIR) images (A, 1, 3, 5, & 7) and axial T1-post gadolinium images are shown (A, 2, 4, 6, & 8). At initial presentation, T2-hyperintensity (A1) was accompanied by linear radial enhancement (A2). These abnormalities receded after initial immunotherapy (A3, 4), but became prominent again during corticosteroid dose taper (A5, 6), receding again after re-initiation of high dose corticosteroid therapy (A7, 8).

Head MR images for 32 of 38 Mayo Clinic patients were available for review (Table 3, and FIGS. 11-13). Abnormalities were most notable on T1-weighted post-gadolinium sequences. A striking pattern of linear radial gadolinium enhancement, extending outward from the ventricles, was observed in 17 patients (53%; FIG. 12, panels A-C; and FIG. 13, Panels A2 and A6). Enhancement was sometimes punctate in appearance (FIG. 12, Panels C and D). A similar radial enhancement pattern was noted in the cerebellum in two patients (FIG. 11, panel D3). Other enhancement patterns observed less frequently included leptomeningeal (7, 22%), serpentine (6, 19%; FIG. 12, panel E) and ependymal (3, 9%, FIG. 12, panel F). MRI diffusion-weighted sequences were normal in all patients evaluated. Seven patients (18%) had normal MRI brain imaging (phenotypes in these patients included dementia, meningitis, cranial neuropathy, encephalitis with optic neuritis, peripheral neuropathy, dysautonomia and epilepsy).

Among 8 patients with clinical evidence of spinal cord involvement and MRI available, 6 had longitudinally extensive (≥3 vertebral segments long) myelitic abnormalities (75%), 1 had a short myelitic lesion, and 1 had normal imaging (2 with longitudinally-extensive lesions had AQP4-IgG coexisting). A further 2 patients with clinical evidence of encephalitis, but not myelitis, had longitudinally-extensive spinal cord lesions. Linear-appearing central canal enhancement (FIG. 11, panels A2, B2, and C2) was noted in 21% of spinal cord MRIs, but more generalized enhancement patterns were encountered also (punctate or patchy) (FIG. 11, panel C2, D2). MRI abnormalities frequently resolved with corticosteroid treatment (FIG. 13). The remaining MRI abnormalities are summarized in Table 3. The radiological appearance prompted consideration of CNS vasculitis (12 patients, 32%). However, magnetic resonance angiograms (n=12) and digital-subtraction cerebral angiograms (n=6) were normal in all patients tested.

Sensitivity and Specificity of GFAP-IgG for Meningoencephalomyelitis is Greater with CSF than Serum Among the 102 patients, 49 had both serum and CSF testing performed; 45 of 49 (92%) were GFAP-IgG positive in CSF, but just 22 of 49 (45%) were positive in serum (p<0.01). The frequency of meningoencephalomyelitis was more common among those with CSF positivity (59/63, 94%) than among those with serum positivity only (24/39, 62%), p<0.001. However, CSF was not available for testing in 35 of those 39 patients.

Meningoencephalomyelitis Diagnosis is Independent of GFAP-IgG Titer

Patients with high titers (reciprocal of last dilution scored positive) in CSF (tissue IFA values>1:32, n=42) or serum (>1:7680, n=41) were as likely to have meningoencephalomyelitis, or limited form, as patients with lower values (CSF≤1:32, n=11; p=1.000; serum≤1:7680, n=13; p=0.512). The GFAP Isoform Specificity of IgG Detected by CBA does not Predict Tissue IFA Titer, Neurological Phenotype, or Cancer Diagnosis IgG reactive with the GFAPα isoform was detected in serum, CSF, or both in all 102 patients. GFAPε-reactive IgG also was detected in 76 patients (81%), and GFAPκ-reactive IgG was detected in 51 patients (54%), all of whom were additionally GFAPε-IgG positive.

Serum GFAP-IgG titers by tissue IFA were similar regardless of GFAP isoform (median titer for patients positive only for GFAPα-IgG, 1:7680, range, 1:120-1:491,520; for those with coexisting GFAPε-IgG, 1:7680, range, 1:120-1:245,760). CSF titers by tissue IFA likewise were similar regardless of GFAP isoform reactivity beyond GFAPα (median titer for patients only GFAPα-positive, 1:64, range, 1:32-1:1024; for those with coexisting GFAPε-IgG, 1:128, range, 1:4-8192).

The frequency of meningoencephalomyelitis diagnosis (or a limited form) was similar among patients with coexisting GFAPε-IgG (46 of 48 patients, 96%) or with GFAPα-IgG only (6 of 7 patients, 86%), p=0.477. The frequency of cancer detection also was independent of the antigen isoform: GFAPα-IgG only positive, 9 of 25 (36%); GFAPα-IgG and GFAPε-IgG both positive, 8 of 27 (30%) and IgGs reactive with all three GFAP isoforms, 18 of 50 (36%).

Oncologic Findings

Thirty-five patients of 102 (34%) had neoplasia. Twenty-four neoplasms detected in 22 patients concurrent with or subsequent to neurological presentation (median, 0.5 months; range 0-60) included: ovarian teratoma, 15 (mature, 13; immature, 1; both immature and mature, 1 patient with bilateral disease); adenocarcinoma, 3 (1 each of endometrium, esophagus and kidney), glioma, 2; and 1 each of head and neck squamous cell carcinoma, multiple myeloma, pleomorphic adenoma of parotid, and carcinoid. Eighteen historical neoplasms recorded in 14 patients (median, 72 months; range 3-192) were: prostate adenocarcinoma, 3; Hodgkin's lymphoma, 2; lung carcinoma, 2; colon adenocarcinoma, 2; melanoma, 2; and 1 each of mature ovarian teratoma, ovarian adenocarcinoma, nasopharyngeal carcinoma, chronic lymphocytic leukemia, renal cell carcinoma, breast ductal carcinoma in situ, and urothelial bladder carcinoma.

Two patients with biopsy-proven gliomas had GFAP-IgG detected during neurological evaluation (choroid plexus glioma, 1; astrocytoma, 1). Neoplasms were considered causal of encephalopathic symptoms in both. One patient had GFAP-IgG positivity in serum (GFAPα-IgG and GFAPε-IgG; IFA titer, 1:122880), but CSF was not evaluated. The other patient had GFAPα-IgG positivity in CSF only (IFA titer, 1:32).

Infectious and Immunodeficiency Accompaniments

Eleven of 38 Mayo Clinic patients (29%) had prodromal flu-like systemic symptoms immediately preceding neurologic presentation, 5 of whom had symptoms of infection (affecting upper respiratory tract, 2; lower respiratory tract, 1 (pneumococcal pneumonia), urinary tract, 1; and prostate, 1). Two further patients, evaluated outside Mayo Clinic, with dysregulated T lymphocyte function developed encephalitis. One patient had chronic HIV/AIDS infection. The other patient with melanoma had received ipilimumab (monoclonal antibody antagonist of cytotoxic T-lymphocyte-associated protein 4 (CTLA-4)).

Coexisting Neural Autoantibodies

NMDA-R-specific IgG detected in CSF, 22 of 102 (22%), was the most common autoantibody coexisting with GFAP-specific IgG. AQP4-specific IgG was the next most common, detected in serum or CSF depending on specimen availability in 10 patients (10%). Teratoma was detected in 5 of 7 patients who had both NMDA-R-specific IgG and AQP4-specific IgG coexisting (71%), 8 of 15 patients with only NMDA-R-specific IgG coexisting (53%), and 2 of 3 patients with only AQP4-specific IgG coexisting (66%, neither patient had CSF available for NMDA-R-IgG testing). Just one teratoma patient of 15 (7%) was seronegative for both NMDA-R IgG and AQP4-IgG. Neurological syndromes were: encephalitis in all who had both NMDA-R-IgG and AQP4-IgG coexisting; encephalitis (13), encephalomyelitis (1) and meningoencephalomyelitis (1) in those with only NMDA-R-specific IgG coexisting; and encephalomyelitis (2) and neuromyelitis optica (NMO, 1) in those with only AQP4-IgG coexisting.

Other neural antibodies coexisting with GFAP-specific IgG were reactive with: glutamic acid decarboxylase 65 (GAD65), 7 (median value, 0.17 nmol/L, range, 0.04-4.16; normal≤0.02); striated muscle antigens, 5 (median value, 1:480, range, 120-61440; normal≤120); ganglionic acetylcholine receptor, 4 (median value, 0.09 nmol/L, range, 0.04-0.22; normal≤0.02); P/Q-type calcium channel, 3 (median value, 0.08 nmol/L, range, 0.03-0.11; normal≤0.02); and voltage-gated (Kv1) potassium channel-complex, 2 (0.05 and 0.06 nmol/L; normal≤0.02 (neither patient was Lgi1 or CASPR2 IgG-positive).

Treatment Response and Outcome

The details of treatment responses and outcome are summarized in Tables 2 and 4. Median follow-up duration for the 38 Mayo Clinic patients was 20 months (range, 0-174). Of 26 patients with meningoencephalomyelitis, or limited form, 13 had a relapsing course, 7 had a monophasic course, and 6 had progressive disease despite treatment. Two patients had spontaneous improvement without treatment. Long term (≥24 months) treatment details were available for 9 Mayo Clinic patients. Three of these had co-existing NMDA-R-

IgG detected and were treated with intravenous corticosteroids, 3; oral prednisone, 2; plasma exchange, 1; mycophenolate mofetil, 1; and azathioprine, 1. One patient relapsed during tapering of steroid dose two months after symptoms onset. All 3 patients were eventually weaned off of all steroids successfully without known subsequent relapse.

The remaining 6 Mayo Clinic patients with GFAP-IgG positivity, without coexisting AQP4-IgG or NMDA-R-IgG (median treatment time, 54 months; range, 24-144) all had encephalitis with or without meningeal or myelitic findings. These patients were treated with intravenous corticosteroids, 6; oral steroids, 6; mycophenolate mofetil, 5; and azathioprine, 2. Relapses occurred in 3 patients not taking a steroid-sparing drug when reduction of steroid doses were attempted (median of 1.5 relapses; range 1-5, occurring at prednisone doses <20 mg per day) and in 3 patients when steroid sparing immunotherapy was discontinued. Clinical relapses were frequently accompanied by recurrent gadolinium enhancement on MRI and elevated CSF white cell counts, with further remission on restarting steroids (FIG. 13). All 6 patients were in remission and taking steroid-sparing maintenance immunotherapy at last follow up, 5 of whom had discontinued prednisone. Two patients required increases in mycophenolate dosing from 2000 mg/day to 2500 or 3000 mg/day to overcome steroid-dependency.

These results demonstrate that the median symptom-onset age of autoimmune GFAP astrocytopathy, a novel meningoencephalomyelitis, was 44 years (range, 8-103). Men and women were not differentially affected. The predominant phenotype (81%) was inflammation of meninges, brain or spinal cord, or all three (meningoencephalomyelitis). Striking patterns of enhancement on brain MRI were radial (53%), leptomeningeal (22%), serpentine (19%), or ependymal (9%). Though cases frequently mimicked vasculitis, angiography was uniformly negative, and spinal imaging frequently demonstrated longitudinally-extensive myelitic lesions. Diverse neoplasms encountered were found prospectively in 22%.

Teratoma was most common and was predicted based on the coexistence of both NMDA-R-IgG and AQP4-IgG (71%). Highest sensitivity and specificity for the meningoencephalomyelitic phenotype was observed for CSF testing (92% and 94%, respectively) and for GFAPα-IgG (100% and 96%). Positivity for GFAPε-IgG (81%) and GFAPκ-IgG (54%) was common, but not associated with specific neurological or oncological phenotypes. Six Mayo Clinic patients with prolonged follow-up had brisk corticosteroid response, but required additional immune-suppression to overcome steroid-dependency. Rare positivity was encountered in serum controls by tissue-based assay (0.5%) and cell-based assay (1.5%), though none was positive by both assays. All CSF controls were negative by both assays.

These results demonstrate that GFAP auto-antibodies (GFAPα-IgG), when detected in CSF, is highly specific for a common steroid-responsive autoimmune CNS disorder, sometimes with paraneoplastic cause. These results also demonstrate autoimmune GFAP astrocytopathy patients with NMDA-R auto-antibodies (NMDA-R-IgG) and AQP4 auto-antibodies (AQP4-IgG) are likely to have underlying teratoma. Additional oncological accompaniments of GFAP-IgG included adenocarcinomas (e.g., adenocarcinoma of endometrium, stomach, esophagus, or kidney), glioma, head and neck squamous cell carcinoma, multiple myeloma, pleomorphic parotid adenoma, and carcinoid tumor.

Example 3—Autoimmune GFAP Astrocytopathy: Prospective Evaluation of 90 Patients in 1 Year The following was performed to prospectively evaluate the use GFAPα-IgG testing in both adults and children. Briefly, serum and CSF specimens were evaluated over 1 year by indirect immunofluorescence assay for the characteristic GFAP-IgG staining of murine tissues, followed by GFAPα-IgG cell based assay confirmation. Multiple disease controls were tested. Demographic and clinical data were reviewed.

In summary, meningoencephalomyelitis, or limited form, was the most common phenotype (80%). MRI demonstrated patchy, irregular/peri-radial parenchymal enhancement with or without leptomeningeal enhancement in 48.6% patients. Almost all of these patients had inflammatory CSF (93.1%): elevated CSF protein>50 mg/dL (81.9%) or lymphocytic pleocytosis (86.1%). Ten patients had malignancy. All but 1 of 68 CSF GFAPα-IgG positive patients had meningoencephalomyelitis. Clinical phenotypes were diverse among patients that were positive in serum only. Among cases with both serum and CSF samples available (54), where only 1 specimen type was positive, CSF had better positive predictive value for meningoencephalomyelitis (100% vs 0%). Adult and pediatric meningoencephalomyelitis presentations were similar. The majority of patients responded well to first-line immunotherapy (usually corticosteroids, 66.7%). Refractoriness to first-line immunotherapy was associated with presence of co-existing NMDA-R IgG (50% vs 6.8%, p<0.001) or malignancy (27.8% vs 2.2%, p=0.002). Among patients (25) with follow-up information, 28% had relapses. Four patients died; three due to severe encephalitis.

CSF GFAPα-IgG is a specific autoimmune meningoencephalomyelitis biomarker, usually with favorable corticosteroid response. Immunotherapy refractoriness should prompt evaluation for co-existing NMDA-R IgG or malignancy.

Methods

Serum and CSF specimens (CSFs) were prospectively evaluated by indirect immunofluorescence assay (IFA) for the characteristic GFAP-IgG staining of murine tissues, with a confirmation as determined by a GFAPα-transfected cell based assay (CBA). Physicians were contacted to obtain additional specimens (where only one of serum or CSF had been submitted) and clinical information. Other neural antibodies were evaluated as described elsewhere (McKeon et al., *Acta Neuropathol.*, 122:381-400 (2011); Toledano et al., *Neurology*, 82:1578-1586 (2014); and Zalewski et al., *Muscle Nerve*, 54:220-227 (2016)).

Disease controls (281 total) included patients with: polymerase chain reaction-confirmed herpes viral encephalitis cases (56 CSFs), chronic lymphocytic inflammation with pontine perivascular enhancement responsive to steroids (CLIPPERS, 19 serums), traumatic brain injury (TBI, 5 CSFs, 34 serums), type I diabetes (30 serums), relapsing remitting multiple sclerosis (MS, 41 CSFs), aquaporin-4 (AQP-4) autoimmunity (15 CSFs), NMDA-R encephalitis (27 CSFs), astrocytoma (5 CSFs, 22 serums), and hereditary leukodystrophy (4 CSFs, 23 serums). Nominal and interval variables were analyzed by $\chi^2$ and Mann-Whitney test, respectively.

Results

Control Subjects

One CSF (and no other control specimens) had GFAPα-IgG detected (a patient with AQP4 autoimmunity coexisting).

Patients

Clinical-Serological Correlations

Specimens from 103 patients (45 of 107 serums and 69 of 197 CSFs tested) were IFA positive, confirmed by GFAPα CBA. Clinical information was obtained for 90 of 103 patients. After requesting additional serums or CSFs for GFAPα-IgG positive patients with only one specimen type submitted initially, 54/90 had both serum and CSF available, 18/90 had only CSF, and 18/90 had only serum.

All 68 patients with GFAPα-IgG detected in CSF (median endpoint value, 32; range, 4-1024), bar 1 with transient weakness without additional diagnostic information available, had meningoencephalomyelitis (FIGS. 14A, 14B, 14C, 14D and 14F). One patient, exemplified by FIG. 14D, was a radiological mimic of hereditary leukodystrophy (untreatable). GFAP-IgG antibody positivity was diagnostic of an autoimmune disease and indicated treatment with immune therapy. This was regardless of serum GFAPα-IgG positivity (N=24), negativity (N=26), or unavailability (N=18). Twenty-two patients had GFAPα-IgG positivity detected in serum only (median titer, 960; range, 240-7680). Four of those GFAPα-IgG negative in CSF had epilepsy (2), ataxia and dysautonomia (1), or small fiber neuropathy (1). The remaining 18 serum positive patients did not have CSF available. Their diagnoses were meningoencephalomyelitis (5), peripheral neuropathy (7), ataxia (7), and dysautonomia (3).

Figure 15A:
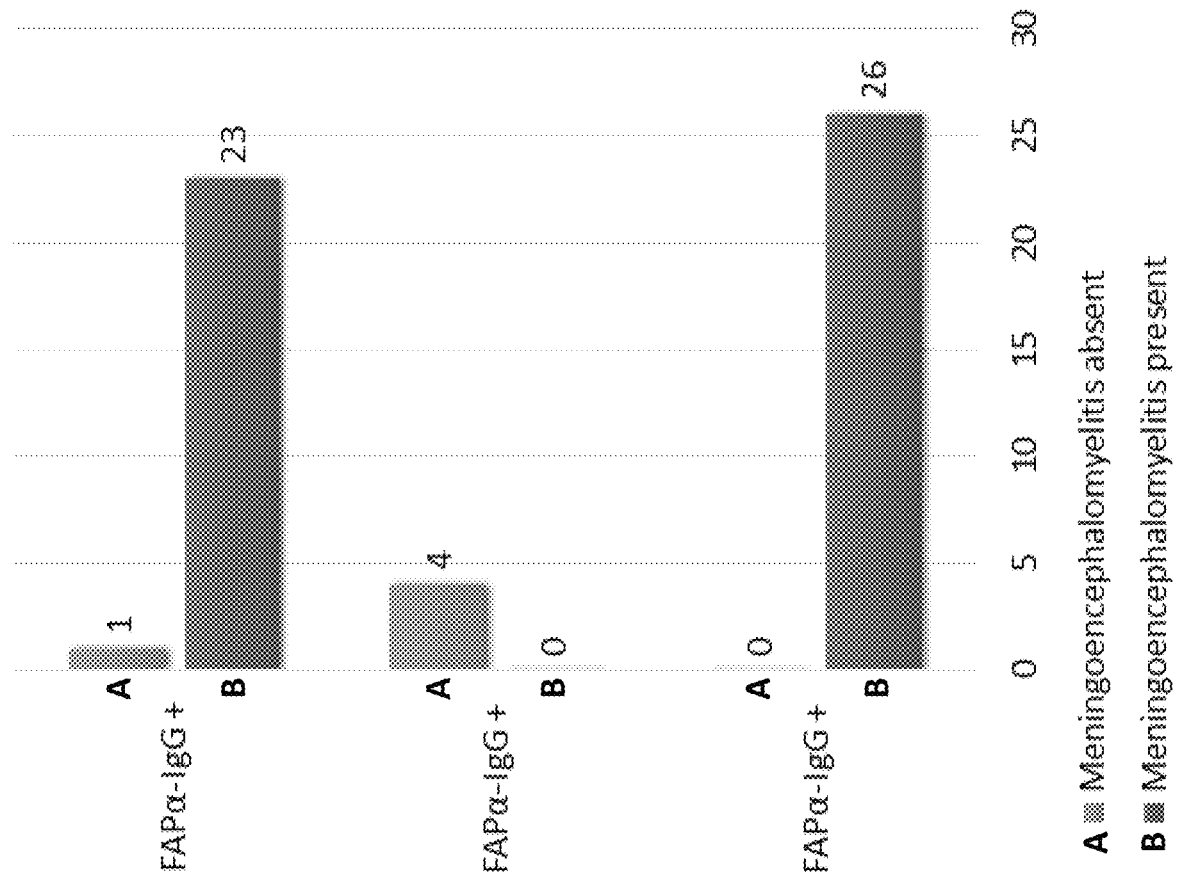
FIGS. 15A-B. Association of meningoencephalomyelitis phenotype with GFAPα-IgG positivity in CSF, serum, or both CSF and serum (FIG. 15A). Response to first-line immunotherapy (63 patients) with or without co-existing NMDA-R IgG and malignancy (FIG. 15B). GFAP, glial fibrillary acid protein; CSF, cerebrospinal fluid; NMDA-R N-methyl-d-aspartate receptor.
Figure 15B:
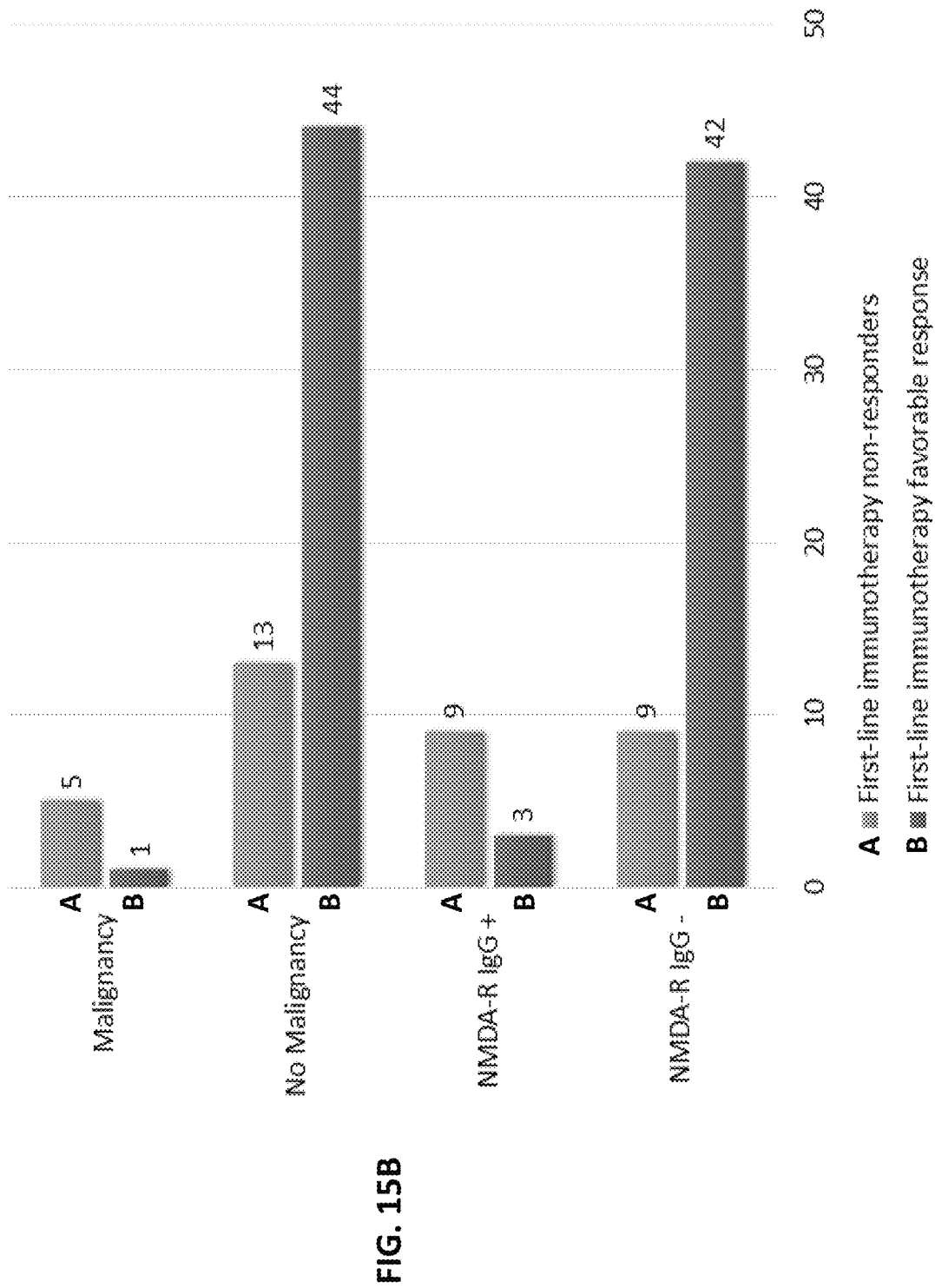

Among 54 patients with both serum and CSF evaluated, 26 were CSF GFAPα-IgG positive, 4 were serum GFAPα-IgG positive, and 24 were positive in both. Positive predictive values for GFAPα-IgG were as follows: both CSF and serum positive, 95.8%; only CSF positive, 100%; and only serum positive 0% (FIG. 15A).

Meningoencephalomyelitis Patients

Among 72 patients with meningoencephalomyelitis, median symptom onset age was 50 (range, 8-86), and the male:female ratio was 38:33. Meningoencephalomyelitis phenotypes included meningoencephalitis without myelitis (39), meningoencephalitis with myelitis (27), and myelitis only (5). Headache and neck stiffness were common (62.5%), as were one or more of rhinorrhea, sore throat, fever, and cough (40.3%). The majority (93.1%) were initially suspected to have infectious meningoencephalitis; all were treated with antimicrobial therapies. Ataxia (37.5%) and autonomic dysfunction (22.2%) commonly coexisted with meningoencephalomyelitis. In a minority, brainstem dysfunction (eye movement disorders, 15.3%), epilepsy (11.1%), and peripheral neuropathy (2.8%) were encountered.

Most patients tested had inflammatory CSF (67/72, 93.1%) as characterized by elevated CSF protein >50 mg/dL (59/72, 81.9%; median, 69.5 mg/dL; range, 0-287) and lymphocyte-predominant elevated white blood cells (62/72, 86.1%; median 40 cells/dL; range, 0-800). MR head imaging revealed patchy irregular or peri-radial parenchymal enhancement with or without leptomeningeal enhancement in 35/72 (48.6%) patients (FIGS. 14A and 14B). Significant peri-ventricular T2 or fluid attenuated inversion recovery signal changes were observed in 40.3% cases (29/72). Intensive care unit (ICU) admission was common at initial presentation (32/72, 44.4%). A subset of these (12/32, 37.5%) required intubation for airway protection.

The meningoencephalomyelitis phenotypes, serological and other paraclinical findings in 10 children, seemed consistent with the adults (Table 5).

TABLE 5

Clinical, laboratory, and imaging characteristics of pediatric cases with serum and/or CSF GFAPα-IgG.

| Age (years) | Clinical presentation | CBA positivity | IFA (titer) | MRI characteristics | CSF findings | Immuno-modulatory therapy | Response to immune-therapy |
|---|---|---|---|---|---|---|---|
| 3, M | Refractory epilepsy | Serum+, CSF− | Serum+ (960), CSF− | Normal | Normal | none | — |
| 8, F | Meningoencephalitis, aphasia, coexisting NMDA-R IgG | Serum−, CSF+ | Serum−, CSF+ (8) | Lepto-meningeal enhancement | Inflammatory (protein 55 mg/dl, TNC^: 159/dl) | IVMP, PLEX, RTX | Favorable** |
| 9, M | Autonomic dysfunction, ataxia | Serum+, CSF− | Serum (480), CSF− | Normal | normal | None | — |
| 10, F | Meningoencephalitis | Serum+, CSF+ | Serum−, CSF+ (4) | Lepto-meningeal and patchy parenchymal enhancement | Inflammatory (protein 47 mg/dl, TNC^: 71/dl) | IVMP | Favorable* |
| 10, F | Ataxia | Serum+, CSF# | Serum (1920), CSF# | Normal | Not obtained | none | — |
| 10, M | Menignoencephalo-myelitis, autonomic dysfunction | Serum−, CSF+ | Serum−, CSF+ (16) | Lepto-meningeal and patchy parenchymal enhancement | Inflammatory (protein 60 mg/dl, TNC^: 155/dl) | IVMP | Favorable* |
| 12, M | Meningitis, myelopathy | Serum#, CSF+ | Serum#, CSF+ (8) | Normal | Inflammatory (protein 211 mg/dl, TNC^: 12/dl) | IVMP, IVIG | Favorable* |
| 13, M | Meningoencephalitis | Serum#, CSF+ | Serum#, CSF+ (32) | Normal | Inflammatory (protein 287 mg/dl, TNC^: 148/dl) | IVMP, IVIG | Favorable* |

TABLE 5-continued

Clinical, laboratory, and imaging characteristics of pediatric cases with serum and/or CSF GFAPα-IgG.

| Age (years) | Clinical presentation | CBA positivity | IFA (titer) | MRI characteristics | CSF findings | Immuno-modulatory therapy | Response to immune-therapy |
|---|---|---|---|---|---|---|---|
| 15, M | Menignoencephalo-myelitis | Serum+, CSF+ | Serum−, CSF+ (32) | Normal | Inflammatory (protein 65 mg/dl, TNC^: 51/dl) | IVMP | Favorable* |
| 15, F | Menignoencephalitis, co-existing NMDA-R IgG | Serum+, CSF+ | Serum (480), CSF+ (32) | Parenchymal enhancement and T2/FLAIR hyperintensity in parietal lobe | Normal | IVMP, Rituximab | Favorable** |

*Response to first line immunomodulatory therapy (IV MP, IVIg, PLEX)
**response following administration of second-line immunotherapy (e.g., rituximab, mycophenolate mofetil, cyclophosphamide)
quantity insufficient or sample not available for testing
NMDA-R, N-methyl-d-aspartate-receptor
TNC: total number of nucleated cell
^lymphocytic predominant Ten patients (9 adults with meningoencephalomyelitis, 1 with peripheral neuropathy) were diagnosed with neoplasia, ovarian teratoma being most common (3 patients). Other neoplasms included ovarian adenocarcinoma (1), lung small cell carcinoma (1), lung adenocarcinoma (1), B-cell lymphoma (1), bladder urothelial carcinoma (1), nasopharyngeal squamous cell carcinoma (1), and metastatic adenocarcinoma of unknown primary (1). Co-existing antibodies included NMDA-R IgG (12, 2 patients had ovarian teratoma), aquaporin-4-IgG (3, 1 had ovarian teratoma), ANNA-1 (1, lung small cell carcinoma), PCA-1 (1, ovarian adenocarcinoma), LGI-1-IgG (1), CASPR2-IgG (1), and GAD65-IgG (1).

Treatment information was available for 63 patients with meningoencephalomyelitis. The majority who received immunotherapy (66.7%, 42/63) responded well to first-line immunotherapy (high dose corticosteroids 60/63, IVIg 3/63). More prolonged immune suppression was employed in 20 patients (rituximab, 12 patients; mycophenolate mofetil, 4 patients; cyclophosphamide, 2 patients; or oral prednisone, 2 patients).

Among 25 patients with meningogoencephalomyelitis with follow-up data available (median 5 months, range 2-36 months), 28% (7/25) relapsed. The presence of leptomeningeal and/or punctate parenchymal gadolinium enhancement was associated with an acute progressive course leading to ICU admission (59.5% vs 26%, p=0.002) and intubation (27.8% vs 8%, p=0.014). Refractoriness to first-line immunotherapy was associated with NMDA-R IgG coexisting (50% vs 6.8%, p<0.001) and neoplasia diagnosis (27.8% vs 2.2%, p=0.002). Four patients died, attributable to progressive encephalitis (3 patients, 2 of which were untreated) or metastatic adenocarcinoma (1 patient).

The results provided herein demonstrate that nearly all patients (67/68) in whom GFAPα-IgG was detected in CSF had a meningoencephalomyelitis clinical phenotype. Serum antibody positivity in the absence of CSF GFAP-α IgG was less specific. Indeed, among four patients with serum positivity in the absence of CSF positivity, none had meningoencephalomyelitis. These results also demonstrate that pediatric cases (10 pediatric cases) exhibited clinical presentations, test findings, and responses to treatment that were similar to those of the adult patients.

In addition, GFAPα-IgG was not detected in any patients with active viral meningoencephalitis, permitting distinction from an autoimmune entity; the initial therapy choice for which (corticosteroids) may exacerbate certain infectious meningencephalitides (Linnoila et al., Neurol. Neuroimmunol. Neuroimmunol., 3:e245 (2016); and Venkatesan et al., Clin. Infect. Dis., 57:1114-1128 (2013)). Specimens from patients with CLIPPERS were also used as controls (all GFAPα-IgG negative also) because that entity can superficially resemble autoimmune GFAP astrocytopathy radiologically (Pittock et al., Brain, 133:2626-2634 (2010)). The results using the CLIPPERS controls demonstrate that GFAP-IgG is specific for autoimmune GFAP astrocyopathy and not a disorder known as CLIPPERs, which superficially mimics GFAP autoimmunity. Additionally, CSF and serum specimens from control subjects with TBI were GFAPα-IgG negative, illustrating the specificity of using GFAP-IgG as detected by tissue IFA and confirmed by GFAPα CBA for autoimmune GFAP astrocytopathy, as opposed to traumatic brain injury in which low titer GFAP antibodies of questionable specificity have been reported (Flanagan et al., Ann. Neurol., 81:298-309 (2017); and Zhang et al., PLoS One, 9:e92698 (2014)).

Most patients improved after receiving corticosteroids, though 25% relapsed upon treatment cessation. Notably, 3 of 4 untreated patients died, indicating the importance of GFAP-IgG in distinguishing patients with a treatable encephalitis from an untreatable one. In addition to not receiving treatment, or receiving treatment for too short a time, co-existence of NMDA-receptor IgG and the presence of cancer were associated with poor clinical response. For relapsing patients, further corticosteroid treatment at high doses for a minimum of 3 months and introduction of a steroid-sparing drug (e.g., mycophenolate mofetil or azathioprine) resulted in favorable outcomes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A kit for identifying a human as having autoimmune glial fibrillary acidic protein (GFAP) astrocytopathy, wherein said kit comprises (a) a first antigen source comprising a human GFAP polypeptide, (b) an anti-human IgG antibody, (c) a human GFAP-specific IgG as a positive control, and (d) a second antigen source comprising a N-Methyl-D-Aspartate receptor (NMDA-R) polypeptide and an aquaporin-4 (AQP4) polypeptide, wherein said second antigen source comprises a cell transfected to express said NMDA-R polypeptide and said AQP4 polypeptide.

2. The kit of claim 1, wherein said first antigen source comprises a cell transfected to express said human GFAP polypeptide.

3. The kit of claim 1, wherein said first antigen source lacks NMDA-R and AQP4 polypeptides.

4. The kit of claim 1, wherein said anti-human IgG antibody is covalently attached to a label moiety.

5. The kit of claim 4, wherein said label moiety is a florescent moiety.

6. The kit of claim 1, wherein said NMDA-R polypeptide is a human NMDA-R polypeptide.

7. The kit of claim 1, wherein said AQP4 polypeptide is a human AQP4 polypeptide.

8. The kit of claim 1, wherein said kit comprises said NMDA-R-specific IgG as a positive control and said AQP4-specific IgG as a positive control.

* * * * *

UNITED STATES PATENT AND TRADEMARK OFFICE
CERTIFICATE OF CORRECTION

PATENT NO. : 12,105,088 B2
APPLICATION NO. : 17/870477
DATED : October 1, 2024
INVENTOR(S) : Vanda A. Lennon et al.

It is certified that error appears in the above-identified patent and that said Letters Patent is hereby corrected as shown below:

On the Title Page

Column 2 (Item (56) Other Publications), Line 2, delete "Tumor Biol," and insert -- Tumour Biol., --.

Column 2 (Item (56) Other Publications), Line 7, delete "Immunoprecipitatior" and insert -- Immunoprecipitation --.

Column 2 (Item (56) Other Publications), Line 13, delete "Enzyme-lined" and insert -- Enzyme-linked --.

Column 2 (Item (56) Other Publications), Line 16, delete "Neurol. Scanc.," and insert -- Neurol. Scand., --.

Signed and Sealed this
Nineteenth Day of November, 2024

Katherine Kelly Vidal
*Director of the United States Patent and Trademark Office*